US011273043B1

(12) United States Patent
Abbasi

(10) Patent No.: US 11,273,043 B1
(45) Date of Patent: Mar. 15, 2022

(54) SYSTEM AND METHOD FOR FUSION OF SACROILIAC JOINT

(71) Applicant: Advance Research System, LLC, Edina, MN (US)

(72) Inventor: Hamid R. Abbasi, Edina, MN (US)

(73) Assignee: Advance Research System, LLC, Edina, MN (US)

( * ) Notice: Subject to any disclaimer, the term of this patent is extended or adjusted under 35 U.S.C. 154(b) by 259 days.

(21) Appl. No.: 16/443,303

(22) Filed: Jun. 17, 2019

Related U.S. Application Data

(60) Provisional application No. 62/861,937, filed on Jun. 14, 2019, provisional application No. 62/801,316, (Continued)

(51) Int. Cl.
*A61B 17/86* (2006.01)
*A61B 17/70* (2006.01)
(Continued)

(52) U.S. Cl.
CPC .......... *A61F 2/30988* (2013.01); *A61B 6/505* (2013.01); *A61B 17/7055* (2013.01); (Continued)

(58) Field of Classification Search
CPC .............. A61B 17/1757; A61B 17/864; A61B 17/7055; A61F 2002/4687; A61F 2/4611
See application file for complete search history.

(56) References Cited

U.S. PATENT DOCUMENTS 4,966,604 A 10/1990 Reiss
5,738,685 A 4/1998 Halm et al.
(Continued)

FOREIGN PATENT DOCUMENTS

WO WO 2005/079682 9/2005
WO WO 2016/168589 10/2016
WO WO 2017/223454 12/2017

OTHER PUBLICATIONS

Medacta International "M.U.S.T. SI Sacro-Iliac Joint Screw System" Medacta International 2017-2018 downloaded from the internet at https://www.medacta.com/EN/must-si last visited Jun. 13, 2018 (3 pages).
(Continued)

*Primary Examiner* — David W Bates
(74) *Attorney, Agent, or Firm* — Christensen, Fonder, Dardi & Herbert PLLC

(57) ABSTRACT

A system for performing a minimally invasive sacroiliac joint fusion. The system may be in the form of a disposable kit, with the components streamlined so that the procedure can be performed in a few minutes. The screw components are self-drilling and self-tapping. The system may deploy blades through the walls of the primary screw which cut away material as the primary screw is set, for denuding the sacroiliac joint. The primary screw is designed bore through and internalize bone tissue in an autografting process. The implant system may include components for packing bone grafting material into the screw to supplement autograft bone tissue internalized in the primary screw during placement. At least one side screw is passed through a head of the primary screw to anchor the head and prevent it from backing out after implantation.

6 Claims, 25 Drawing Sheets

Related U.S. Application Data filed on Feb. 5, 2019, provisional application No. 62/685,605, filed on Jun. 15, 2018.

(51) Int. Cl.

| | |
|---|---|
| ***A61F 2/30*** | (2006.01) |
| ***A61B 17/88*** | (2006.01) |
| ***A61B 34/20*** | (2016.01) |
| ***A61B 6/00*** | (2006.01) |
| *A61F 2/46* | (2006.01) |
| *A61B 17/56* | (2006.01) |

(52) U.S. Cl.

CPC ........ *A61B 17/864* (2013.01); *A61B 17/8615* (2013.01); *A61B 17/8888* (2013.01); *A61B 34/20* (2016.02); *A61B 17/8605* (2013.01); *A61B 17/869* (2013.01); *A61B 17/8685* (2013.01); *A61B 2017/564* (2013.01); *A61B 2017/8655* (2013.01); *A61F 2/4601* (2013.01); *A61F 2/4603* (2013.01); *A61F 2002/30405* (2013.01); *A61F 2002/30593* (2013.01); *A61F 2002/30622* (2013.01); *A61F 2002/30769* (2013.01); *A61F 2002/30777* (2013.01); *A61F 2002/30785* (2013.01); *A61F 2002/30858* (2013.01); *A61F 2002/30995* (2013.01)

(56) References Cited

U.S. PATENT DOCUMENTS 6,030,162 A 2/2000 Huebner
6,063,088 A * 5/2000 Winslow ............ A61B 17/1757 606/86 A
6,280,443 B1 8/2001 Gu et al.
6,402,757 B1 6/2002 Moore, III et al.
7,329,267 B2 2/2008 Weber
7,637,928 B2 12/2009 Fernandez
7,637,954 B2 * 12/2009 Michelson .............. A61F 2/446 623/17.11
7,799,062 B2 9/2010 Crozet
7,892,261 B2 * 2/2011 Bonutti ................. A61F 2/4455 606/279
9,161,763 B2 10/2015 Assell et al.
9,421,109 B2 8/2016 Donner et al.
9,451,986 B2 * 9/2016 Stoffman ............... A61B 17/68
9,566,095 B2 2/2017 Lorio
9,662,158 B2 5/2017 Reiley
9,668,783 B2 * 6/2017 Goel .................. A61B 17/1757
9,833,321 B2 12/2017 Rindal et al.
9,943,340 B2 4/2018 Whipple et al.
2001/0005796 A1 * 6/2001 Zdeblick .............. A61B 17/025 623/17.11
2001/0053914 A1 * 12/2001 Landry ................. A61F 2/4611 606/99
2003/0191469 A1 10/2003 Ralph et al.
2004/0122457 A1 6/2004 Weber
2004/0267269 A1 12/2004 Middleton et al.
2005/0256578 A1 * 11/2005 Blatt .................. A61B 17/1757 623/17.15
2006/0084986 A1 * 4/2006 Grinberg ............... A61F 2/4684 606/86 A
2007/0122764 A1 5/2007 Balfour et al.
2008/0033440 A1 * 2/2008 Moskowitz ........... A61F 2/4465 606/251
2008/0249552 A1 10/2008 Eliachar et al.
2010/0312280 A1 * 12/2010 Overes ............... A61B 17/8038 606/264
2011/0230884 A1 * 9/2011 Mantzaris .......... A61B 17/8625 606/64
2011/0264229 A1 * 10/2011 Donner ............... A61F 2/30988 623/18.11
2012/0296428 A1 * 11/2012 Donner ............... A61F 2/30988 623/17.11
2013/0053964 A1 * 2/2013 Talwar .................... A61F 2/442 623/17.16
2013/0123923 A1 * 5/2013 Pavlov ................... A61B 17/70 623/17.16
2014/0046383 A1 * 2/2014 Asfora ............... A61B 17/1615 606/304
2014/0088707 A1 * 3/2014 Donner .............. A61B 17/0218 623/17.11
2014/0142635 A1 5/2014 Purcell et al.
2014/0296982 A1 * 10/2014 Cheng ................... A61F 2/4455 623/17.16
2015/0012051 A1 1/2015 Warren et al.
2015/0018952 A1 1/2015 Ali
2015/0250612 A1 9/2015 Schifano et al.
2017/0189204 A1 * 7/2017 Riemhofer ............ A61F 2/4611

OTHER PUBLICATIONS

Amedica US Spine "Designed for use in degenerative procedures preference 2 Spine System Powered by Tercet Triple-lead Screws" (2011) 2 pages.

Images from L&K Biomed downloaded from internet at http://Inkbiomed.co.kr as of Aug. 11, 2021 (admitted prior art) (pre Jun. 15, 2018).

* cited by examiner

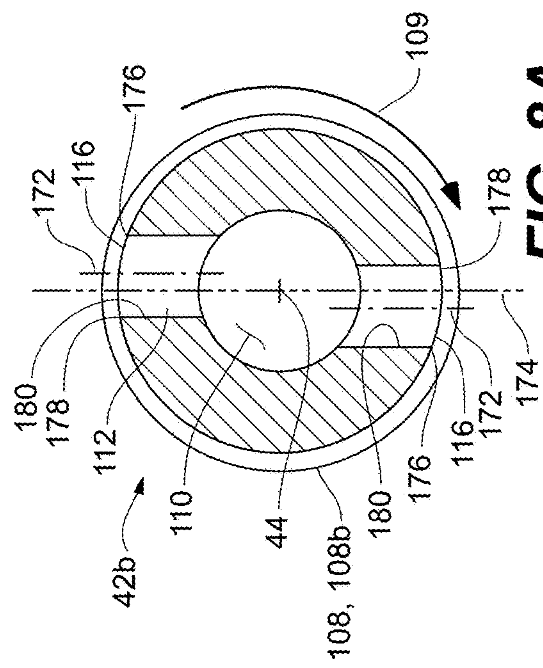
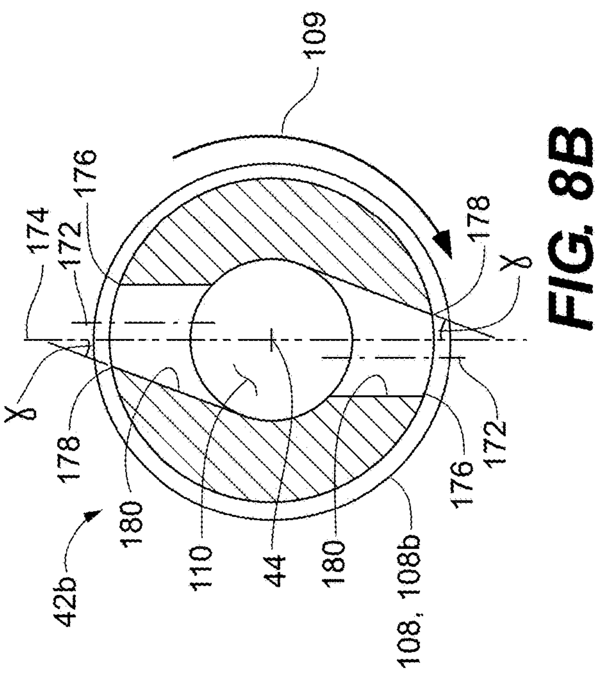
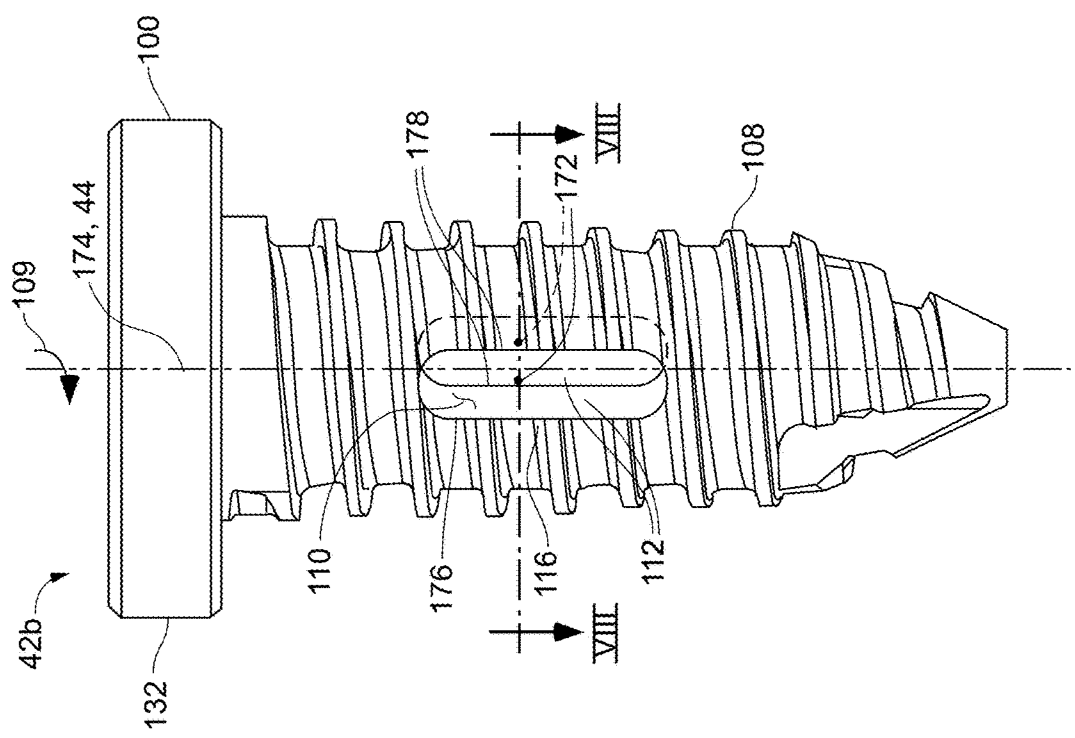

42e
42d
44
132
100
D
d
192
108e
108d
194
105
107
Θ2
198, 198e
198, 198d
196
LP
LD

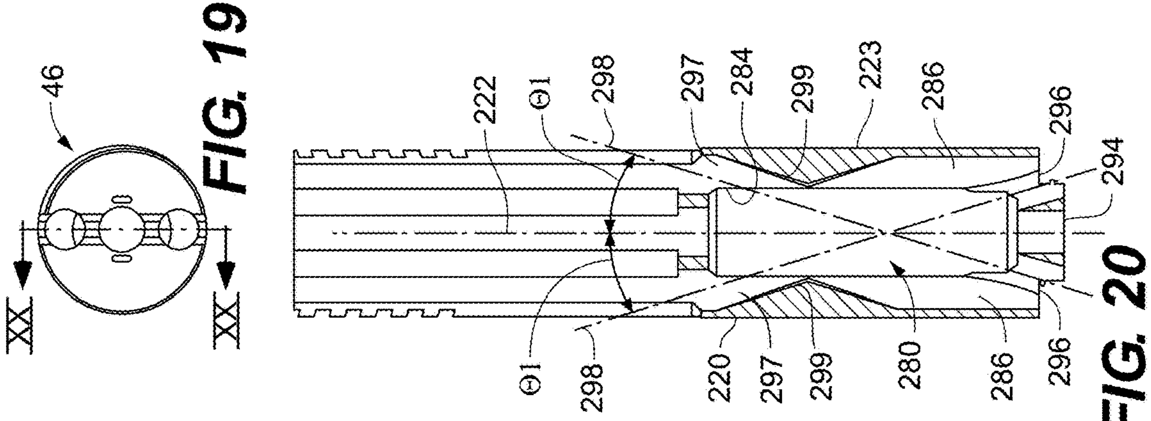
FIG. 19
FIG. 20
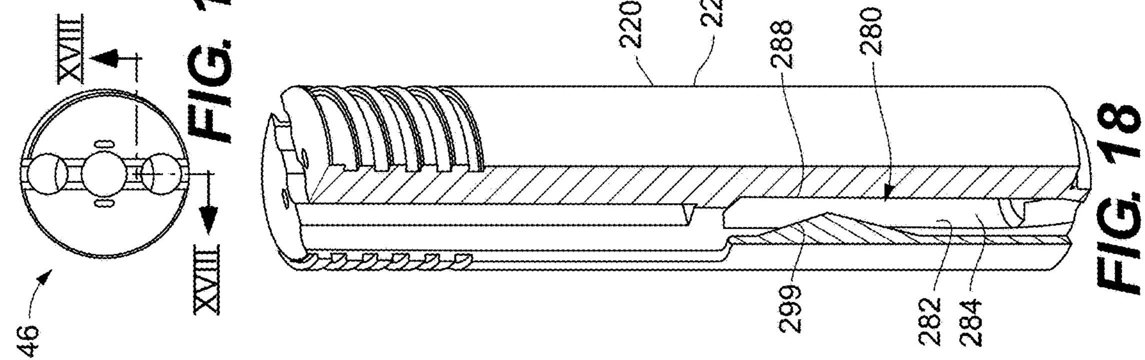
FIG. 17
FIG. 18
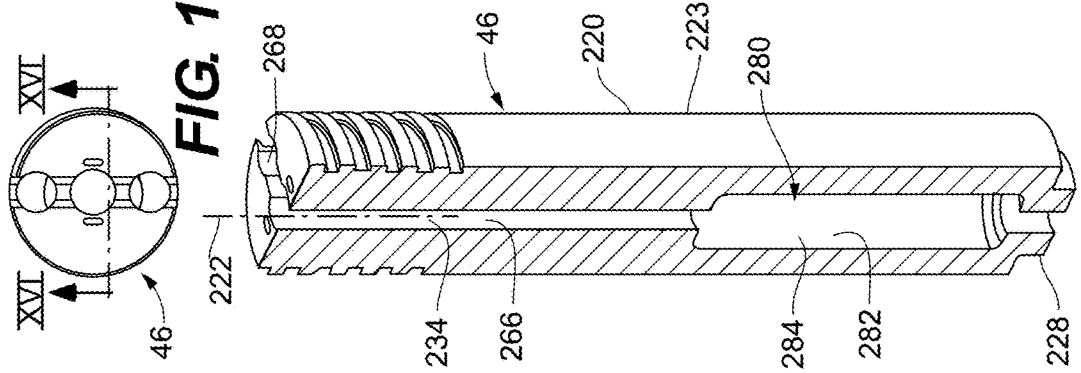
FIG. 15
FIG. 16
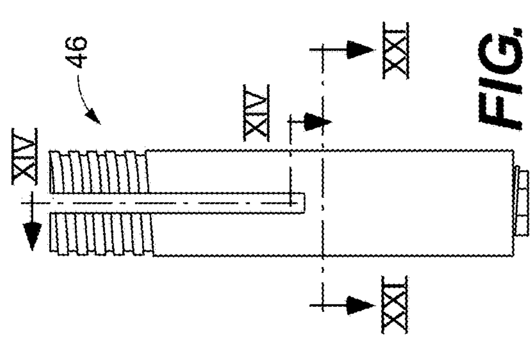
FIG. 13
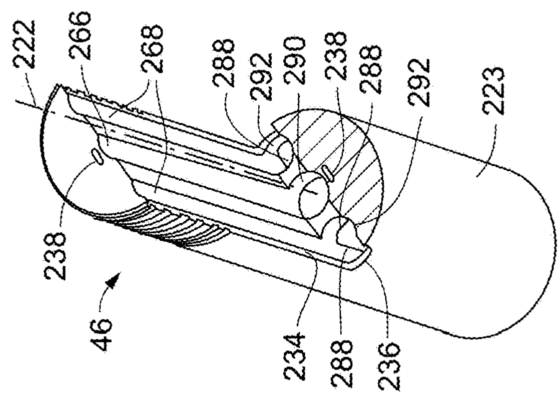
FIG. 14

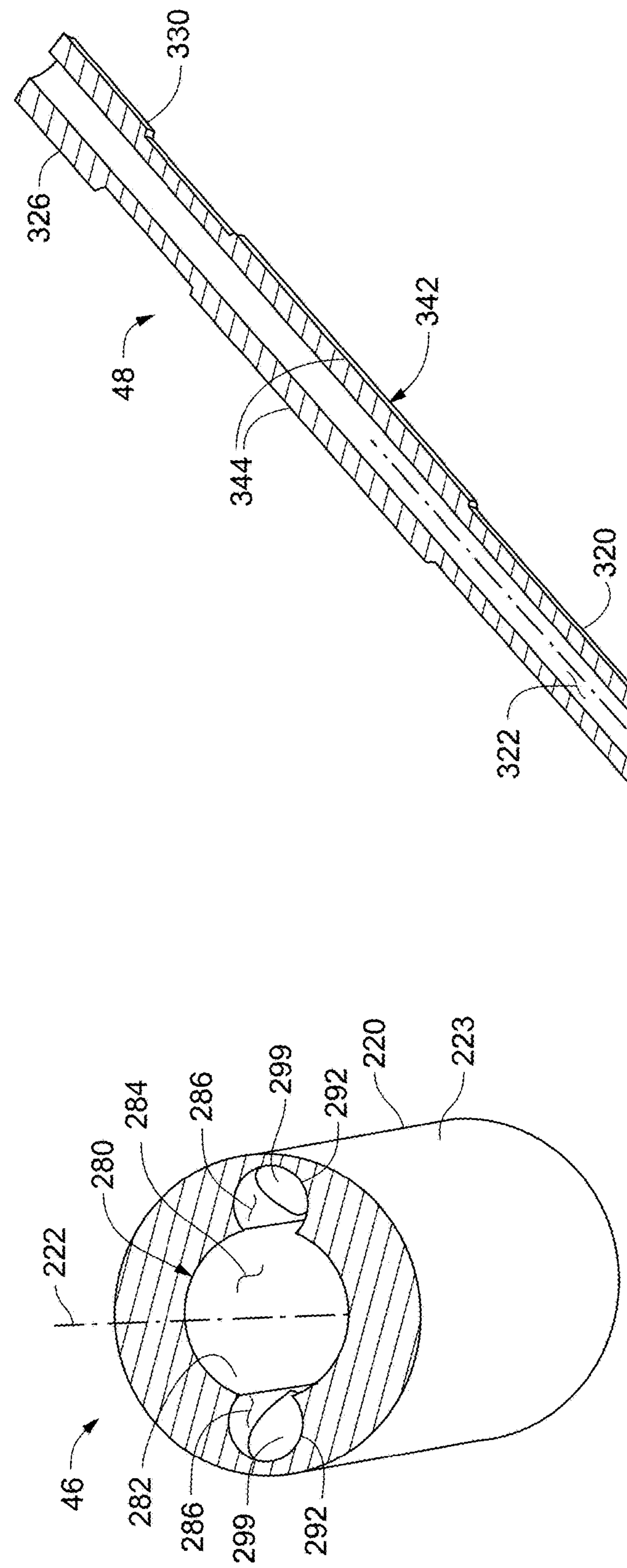
48
326
330
342
344
320
322
324
334
332
46
222
280
284
286
299
292
220
223
282
FIG. 21
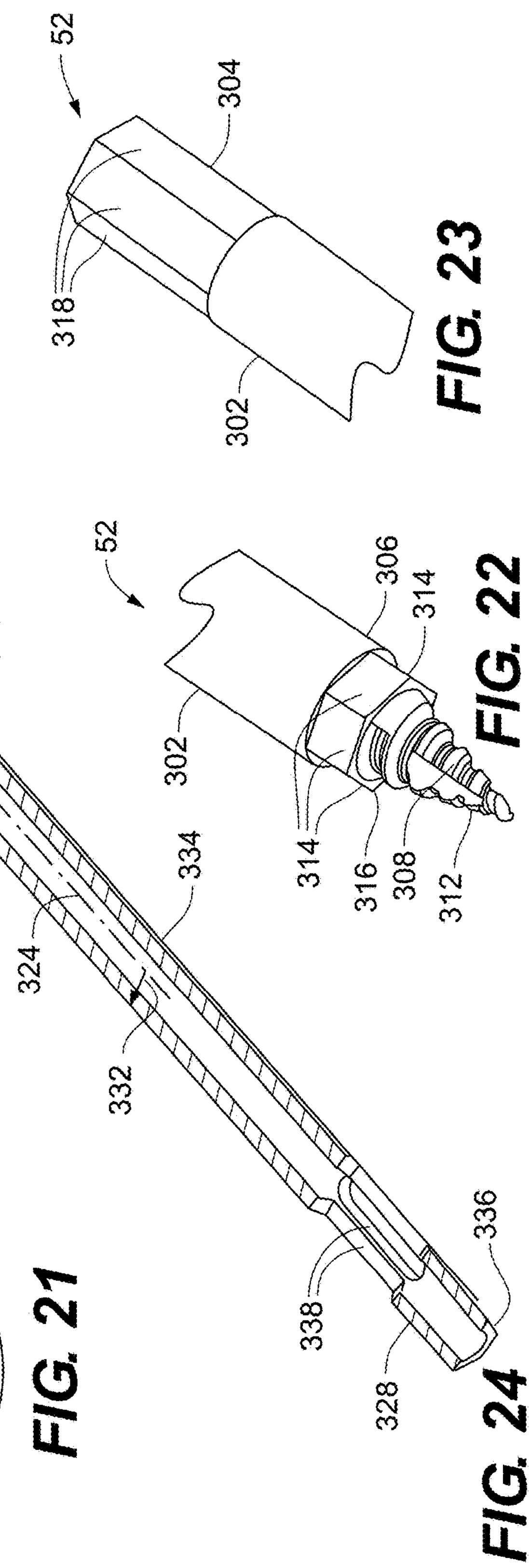
52
304
318
302
FIG. 23
306
314
316
308
312
FIG. 22
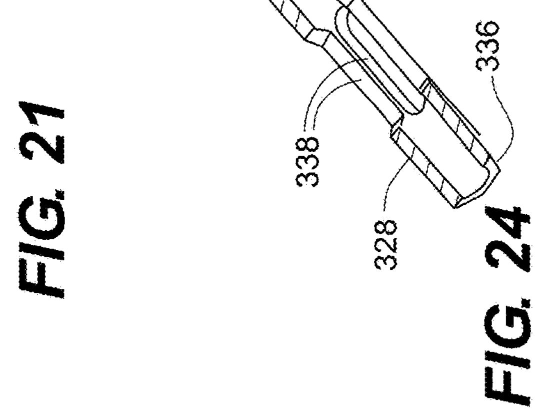
336
338
328
FIG. 24

88
504
514
516
502
518
512
528
526
506
508

538
532
506
508
518
516
502
88
526
528
522
504
508

SYSTEM AND METHOD FOR FUSION OF SACROILIAC JOINT

RELATED APPLICATIONS

This application claims the benefit of U.S. Provisional Patent Application No. 62/685,605, filed Jun. 15, 2018, U.S. Provisional Patent Application No. 62/801,316, filed Feb. 2, 2019, and U.S. Provisional Patent Application No. 62/861,937, filed Jun. 14, 2019, the disclosures of which are incorporated by reference herein in their entirety.

FIELD OF THE DISCLOSURE

The present disclosure is directed generally to tools and techniques for bone fusion, and more specifically to apparatuses and methods for fusion of a sacroiliac joint.

BACKGROUND OF THE DISCLOSURE

Products and techniques for fusion of sacroiliac joints are known. Many techniques involve the implantation of a bone screw that extends substantially perpendicular to the joint. Conventional implantation techniques may require about an hour of surgery to perform. Also, the implants have been known to fail, requiring removal of the implanted bone screw and redress of the joint, at considerable cost and discomfort to the patient. An implantation system that reduces surgical time with improved outcomes would be welcomed.

SUMMARY OF THE DISCLOSURE

Various embodiments of the disclosure include an implant system for performing a minimally invasive sacroiliac joint fusion. The system may be in the form of a disposable kit, with the components augmenting a streamlined procedure that can be performed in under ten minutes. The screw components are self-drilling and self-tapping, thus requiring no pre-drilling, and can be performed without cannulation.

Many conventional fusion systems for sacroiliac joints involve pre-drilling a passage through the ilium and into the sacrum at an approach that is substantially normal to the joint. A bone screw is then implanted in the pre-drilled passage. The pre-drilled passage is sized so that a root diameter of the threads of the bone screw cause an interference fit with the pre-drilled passage, while the protruding portions of the thread cut into the bone. The interference fit in addition to the cutting depth of the threads into the bone anchor the bone screw into place. Often, the surgical site is augmented with growth-promoting biologic to promote growth of bone tissue into the void formed by the pre-drilling.

There are certain disadvantages that are inherent to the conventional method described above. First, it is noted that live bone tissue is generally compressible or "spongy", particularly underneath the harder cortical exterior. The threads implanted by the conventional method described above may be readily stripped from such tissue, which can negate the benefit of the implant.

Second, such conventional procedures remove large portions of the pre-drilled bone. As such, conventional procedures do not take full advantage of natural live autograft bone tissue, which is a better growth-promoting substance than other options, such as allograft, synthetic biologic, or xenograft biologic.

Third, conventional procedures can require several surgical approaches and attendant reconfigurations, thereby increasing surgery time. For example, an implantation that involves placement of a primary bone screw plus a pair of side screws to secure the bone screw essentially involves three surgeries: one for placement of the primary screw and one each for placement of the two side screws. The placement of each component requires reconfiguration of the surgical set up to properly align the component.

The implant system of the present disclosure is based on different principles of operation. The bone screw of the disclosed implant system does not require the separate step of pre-drilling a bore for placement of the primary bone screw. Instead, the self-tapping distal tip of the disclosed primary screw acts as a pre-drill. The disclosed implant displaces a significant portion of the bone tissue radially inward, capturing (internalizing) the tissue within an interior chamber of the bone screw. The autograft bone tissue lodged within the bone screw augments the bone growth characteristics of any allograft, xenograft, or synthetic biologic that may be required. In some embodiments, the internally lodged bone tissue sufficiently fills the interior chamber so that additional growth promoting material is not necessary. The operating principle is to utilize more autograft bone tissue than conventional procedures to increase the effectiveness of the fusion and improve surgical outcomes.

The self-tapping aspect of the primary screw also takes advantage of the spongy, compliant nature of the bone tissue by displacing the remaining portion of the tissue radially outward, which compresses the bone within and around the threads. With the threads imbedded in tissue of greater density, the risk stripping or displacement of the bone screw is diminished.

The components of the disclosed system are designed to streamline the placement of the primary screw and one or more side screws with a single approach. That is, the side screw(s) are implanted without need for separate approach(es). Instead, the system provides alignment of the side screw(s) that is referenced to the primary screw.

Some embodiments of the implant system enable the selective deployment of blades through ports formed in the walls of the primary screw to cut away material at selected depths (e.g., from the cartilage between the ilium and sacrum) as the primary screw is set, for denuding the sacroiliac joint. In some embodiments, the implant system includes components for packing bone grafting material into the screw to supplement the autograft bone tissue internalized by the primary screw and distributing into a zone or zones external to the primary screw created by the blades. The zone external to the primary screw may be annular and surround the primary screw. At least one side screw may be passed through a head of the primary screw to anchor the head and prevent it from backing out after implantation. Some embodiments of the side screws implement a passive locking mechanism when mounted to the bone screw that rotationally secures the side screw to prevent back out or loosening.

Structurally, various embodiments of the disclosure are directed to a system for fusion of a sacroiliac joint, comprising a primary screw defining a central axis and defining a side screw port that extends along a side screw port axis, the side screw port axis intersecting the central axis at an acute angle. A side screw selectively couples to the primary screw, and an inserter defining an inserter axis that extends from a proximal end through a distal end, the distal end being selectively coupled to the primary screw. The inserter axis and the central axis of the primary screw are concentric when the inserter is selectively coupled to the primary screw, with the inserter defining a side channel that extends from the proximal end and parallel to and radially offset from the inserter axis. The side channel is accessible from a lateral side of the inserter, the inserter defining a cross passage that extends along a canted axis from the side channel through the egress port, the cross passage intersecting the central axis. In some embodiments, the canted axis of the inserter is concentric with the side screw port axis of the primary screw when the inserter is selectively coupled to the primary screw. In some embodiments, the side channel and the cross passage are configured for passage of the side screw. The primary screw may define an interior chamber that extends along the central axis and defines a first opening about the central axis at a proximal end of the primary screw and a second opening about the central axis at a distal extremity of the primary screw, the second opening being configured to pass a guide rod. In some embodiments, the primary screw defines an elongate side port that passes through a side wall of the primary screw and is in fluid communication with the interior chamber. The side channel may define an arcuate cross section. In some embodiments, the inserter defines an access slot that passes laterally through the inserter and is coplanar with the inserter axis, the access slot bifurcating the proximal end of the inserter into two opposed wall portions. The side channel may be defined on one of the two opposed wall portions.

The disclosed systems of the present application may comprise a flexible blade disposed within the interior chamber of the shaft portion, the flexible blade extending axially and being tangentially aligned with the elongate side port, the flexible blade being configured to extend adjacent to an exterior opening of the elongate side port when in a retracted configuration. The flexible blade may be configured to bow radially outward through the exterior opening of the elongate side port when in a deployed configuration.

Various embodiments of the disclosure are directed to a system for fusion of a sacroiliac joint, comprising a primary screw including a head portion and a body portion concentric about a central axis, the head portion including a flange that defines a side screw port that extends along a side screw port axis, the side screw port defining female threads along the side screw port axis. A side screw including a head having oblong threads is configured to threadably engage the female threads of the side screw port, the oblong threads defining a major axis and a minor axis. The side screw port may define an oblong through hole and the female threads define a circular root diameter, with the female threads defined on opposed side walls of the side screw port. In some embodiments, a minor radius of the oblong defined along the minor axis is centered within the female threads on a first of the opposed side walls of the side screw port, the side screw is in equipoise within the side screw port. The side screw port may extend through an outer diameter surface of the flange to define a gap along an axial length of the flange. In some embodiments, the side screw port axis defines an acute angle relative to the central axis, the acute angle being open to a distal direction of the primary screw.

In various embodiments of the disclosure, a method for implanting a bone screw for fusion of a sacroiliac joint is presented, comprising: providing a kit including a primary screw, an inserter, and a side screw, and providing operating instructions on a tangible, non-transitory medium. In some embodiments, the operating instructions include: coupling the primary screw to a distal end of the inserter; implanting the primary screw into a penetration site of a bone; inserting the side screw into a cross passage that extends through an inserter central through an egress port defined at a distal end of the inserter, and into a side screw port defined on a head portion of the primary screw; and driving the side screw into the bone. In some embodiments, the kit provided in the step of providing the kit includes a side screw driver, and the operating instructions provided in the step of providing operating instructions includes driving the side screw into the bone with the side screw driver. In some embodiments, the kit provided in the step of providing the kit includes a primary screw driver, and the operating instructions provided in the step of providing operating instructions includes using the primary screw driver to implant the primary screw in the step of implanting. In some embodiments, the kit provided in the step of providing the kit includes an elongate flexible blade, and the operating instructions provided in the step of providing operating instructions includes inserting the elongate flexible blade through the inserter and into the primary screw, and applying an axial force on the flexible elongate blade to cause the flexible elongate blade to bow out of a side port defined on the primary screw. The step of applying an axial force on the flexible elongate blade of the operating instructions may be performed while rotating the primary screw into the penetration site of the bone. In some embodiments, the kit provided in the step of providing the kit includes a drive cap, and the operating instructions provided in the step of providing operating instructions includes using the drive cap to apply the axial force during the step of applying the axial force on the flexible elongate blade. The operating instructions provided in the step of providing operating instructions may include threadably engaging the drive cap with a proximal end of the inserter and rotating the drive cap to apply the axial force during the step of using the drive cap.

In various embodiments of the disclosure, a system for fusion of a sacroiliac joint is disclosed, comprising a primary screw including a shaft portion having a side wall concentric about a central axis, the side wall defining external threads, an interior chamber, and a side port, the side port extending through the external threads and being in fluid communication with the interior chamber, the interior chamber being accessible from an opening defined at a proximal end of the shaft portion. A flexible blade disposed within the chamber of the shaft portion, the flexible blade extending axially and being tangentially aligned with the side port, the flexible blade being configured to extend adjacent to an exterior opening of the side port when in a retracted configuration, the flexible blade being configured to bow radially outward through the exterior opening of the side port when in a deployed configuration. The flexible blade may be removable from the interior chamber. A receiving slot may be defined on an interior surface of the side wall, the receiving slot being proximate a distal end of the side port and axially aligned with the side port, the receiving slot being configured to receive the flexible blade. In some embodiments, a flange disposed at the proximal end of the shaft portion and extending radially beyond the side wall, the flange portion defining a side screw port for receiving a side screw. The side screw port may define a side screw mounting axis that is substantially coplanar with the central axis, the side screw mounting axis extending distally at an acute angle relative to the central axis, the acute angle being in a range of 15 degrees to 20 degrees inclusive. In some embodiments, the side screw port breaches an outer diameter surface of the flange that extends an axial length of the flange, so that the side screw port defines a "C-shape" when viewed along the side screw mounting axis. The system may also include a side screw having a head that defines oblong threads, wherein, an inner wall of the side screw port is oblong, defining a major radius and a minor radius, the inner wall defining female threads that are circular about the side screw mounting axis and cuts into the inner wall at the minor radius. In some embodiments, the oblong threads of the side screw rotate into and out of the female threads as the head of the side screw is rotated into the side screw port.

In some embodiments, an inserter having a distal end configured to mate with the primary screw, the inserter including an interior chamber that is in fluid communication with the interior chamber of the primary screw. A plunger assembly may be selectively attachable to a proximal end of the inserter, the plunger assembly including a stem portion that extends from the proximal end of the inserter into the interior chamber of the inserter, the stem portion being configured to push bone grafting material from the interior chamber of the inserter into the interior chamber of the primary screw. In some embodiments, distal end of the inserter defines a side egress port that is concentric about a canted axis, the canted axis defining an acute angle relative to the central axis of the inserter, the side screw port of the primary screw being aligned with the side egress port and concentric about the canted axis. The interior chamber of the inserter may include an interior wall that defines a guide ramp, the guide ramp extending radially inward from the interior wall and extending adjacent and parallel to the canted axis. In some embodiments, the guide ramp, the side egress port, and the side screw port being centered on a plane that extends through the canted axis. In some embodiments of the disclosure, a distal face of a flank portion of the exterior threads is angled in a proximal direction to define an acute angle relative to the central axis of the primary screw. The acute angle may be in a range of 75 degrees to 80 degrees inclusive.

In some embodiments of the disclosure, a primary screw for fusion of a sacroiliac joint is disclosed, comprising a shaft portion having a side wall concentric about a central axis, the side wall defining external threads, an interior chamber, and first and second side ports, each of the first and second side ports extending through the side wall along a respective lateral axis and being in fluid communication with the interior chamber, the shaft portion defining a laterally extending mid-plane that is coplanar with the central axis, each of the first and second side ports being centered about the respective lateral axis, the respective lateral axes being parallel to the laterally extending mid-plane. The shaft portion may define a first axial notch that extends axially from a perimeter of the first side port and a second axial notch that extends axially from a perimeter of the second side port, the first axial notch and the second axial notch extending parallel to the laterally extending mid-plane. In some embodiments, the respective lateral axes are offset relative to the laterally extending mid-plane, the laterally extending mid-plane extending between the respective lateral axes. The respective lateral axes may be coplanar with the laterally extending mid-plane. In some embodiments, each of the first and second side ports include an edge wall that defines an external opening, each edge wall having a leading tangential edge and a trailing tangential edge relative to a rotational direction for setting the primary screw into bone. The trailing edge of each the edge wall may define an acute sweeping angle relative to the laterally extending mid-plane. In some embodiments, wherein the first axial notch and the second axial notch are centered coplanar with the mid-plane. The shaft portion may also define a first tangential notch that extends tangentially from a perimeter of the first side port and a second tangential notch that extends tangentially from a perimeter of the second side port, the first tangential notch and the second tangential notch extending tangentially relative to the laterally extending mid-plane. In some embodiments, the first tangential notch and the second tangential notch are tangentially aligned. The first and second side ports may be elongate in an axial direction.

Various embodiments of the disclosure include a method for rotationally aligning a bone screw for sacroiliac fusion, comprising: providing a bone screw for sacroiliac fusion; and providing instructions on a tangible, non-transitory medium for rotationally aligning the bone screw. The instructions may include: implanting the bone screw for fusion of a sacroiliac joint, the bone screw defining a first lateral side port on a first lateral side of the bone screw and a second lateral side port on a second lateral side of the bone screw; arranging a surgical imaging device to laterally view a central axis of the bone screw, the surgical imaging device being centered about a viewing axis that intersects the central axis of the bone screw. In some embodiments, the bone screw is rotated so that tangential edges of the second lateral side port are visible with the surgical imaging device through the first lateral side port. In some embodiments, the bone screw is rotated so that a first axial notch that extends axially from a tangential edge of the first lateral side port is axially aligned with a second axial notch that extends axially from a tangential edge of the second lateral side port as viewed with the surgical imaging device. In some embodiments, the tangential edges of the second lateral side port extend axially and are parallel to each other. The viewing axis may intersects the central axis at a 90 degree angle. In some embodiments, the second lateral side port is elongate in an axial direction parallel to the central axis. The surgical imaging device may be an x-ray device.

BRIEF DESCRIPTION OF THE DRAWINGS

FIG. 8 is an elevational view of a primary screw having elongated side ports centered about lateral axes that are offset relative to a mid-plane of the primary screw according to an embodiment of the disclosure;

FIG. 8A is a sectional view of the primary screw of FIG. 8 at plane VIII-VIII with elongated side ports having parallel edge walls according to an embodiment of the disclosure;

FIG. 8B is a sectional view of the primary screw of FIG. 8 at plane VIII-VIII with each elongated side port having an inclined edge wall according to an embodiment of the disclosure;

FIG. 13 is side elevational view of the inserter of FIG. 12A identifying cross-sections XIV-XIV and XXI-XXI according to an embodiment of the disclosure;

FIG. 14 is a partial sectional view along cross-section XIV-XIV of FIG. 13 according to an embodiment of the disclosure;

FIG. 15 is an end view of the inserter of FIG. 12A identifying cross-section XVI-XVI according to an embodiment of the disclosure;

FIG. 16 is a sectional view along cross-section XVI-XVI of FIG. 15 according to an embodiment of the disclosure;

FIG. 17 is an end view of the inserter of FIG. 12A identifying cross-section XVIII-XVIII according to an embodiment of the disclosure;

FIG. 18 is a sectional view along cross-section XVIII-XVIII of FIG. 17 according to an embodiment of the disclosure;

FIG. 19 is an end view of the inserter of FIG. 12A identifying cross-section XX-XX according to an embodiment of the disclosure;

FIG. 20 is a sectional view along cross-section XX-XX of FIG. 19 according to an embodiment of the disclosure;

FIG. 21 is a sectional view along cross-section XXI-XXI of FIG. 13 according to an embodiment of the disclosure;

FIG. 22 is an enlarged partial view of a distal end of a guide rod of FIG. 1 according to an embodiment of the disclosure;

FIG. 23 is an enlarged partial view of a proximal end of a guide rod of FIG. 1 according to an embodiment of the disclosure;

FIG. 24 is a perspective longitudinal sectional view of a primary screw driver of FIG. 1 according to an embodiment of the disclosure;

DETAILED DESCRIPTION

Figure 1:
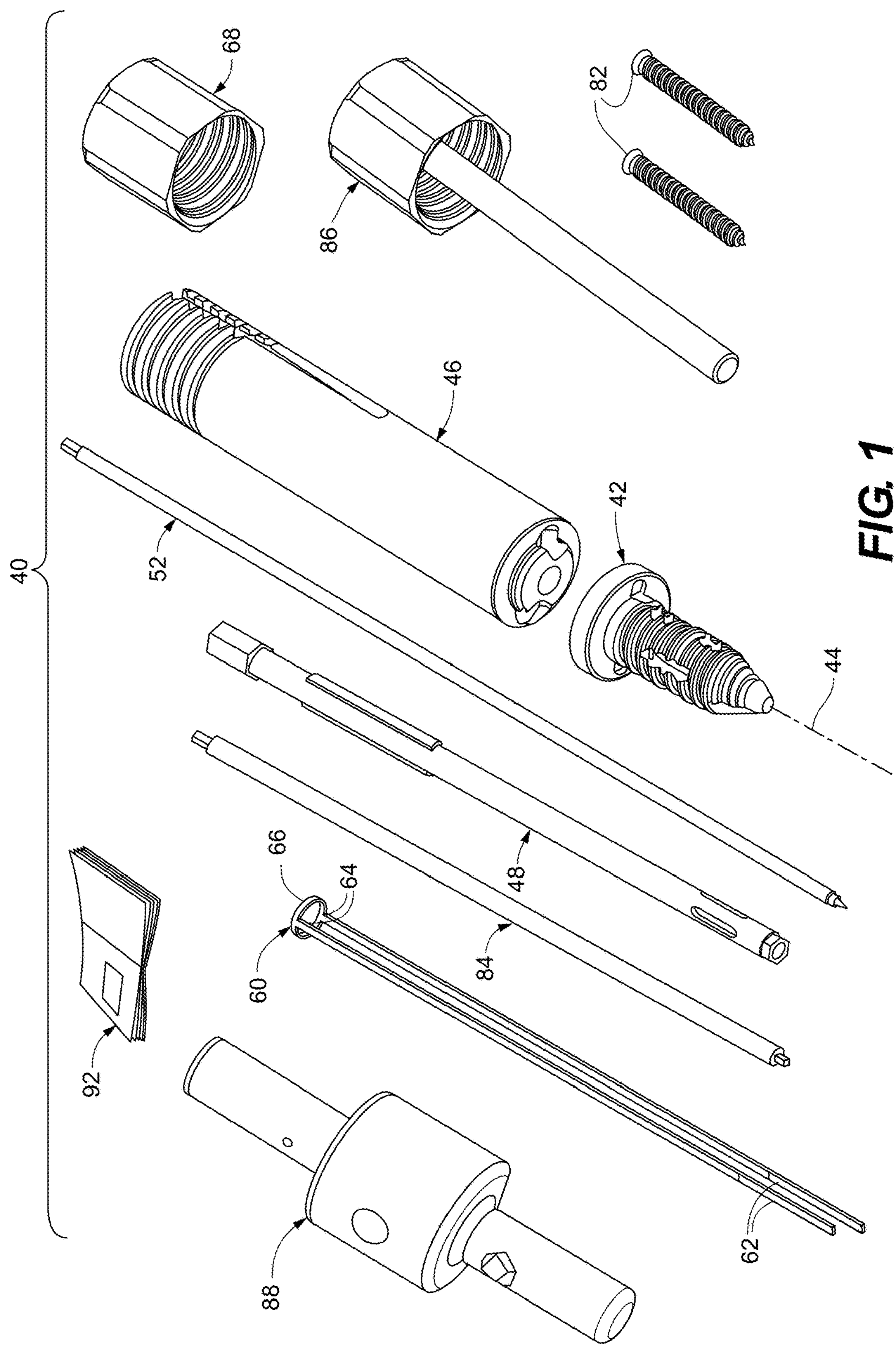
FIG. 1 is a perspective view of components of an implant system for fusion of a sacroiliac joint according to an embodiment of the disclosure.
Figure 2:
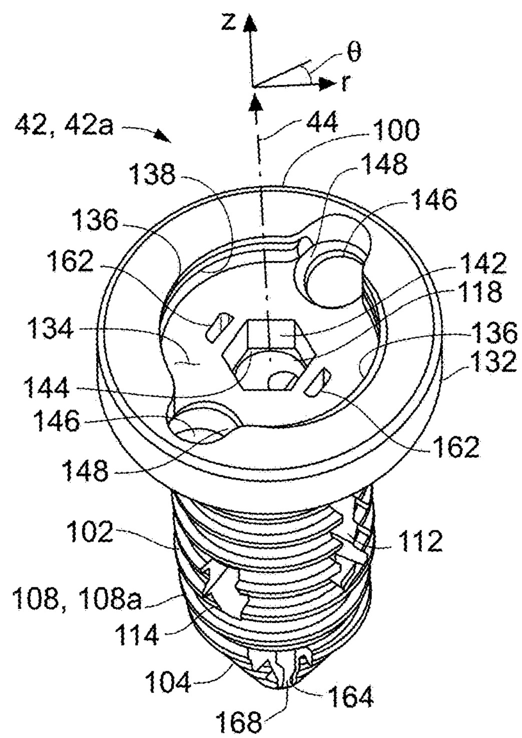
FIG. 2 is a proximal perspective view of a primary screw according to an embodiment of the disclosure.
Figure 3:
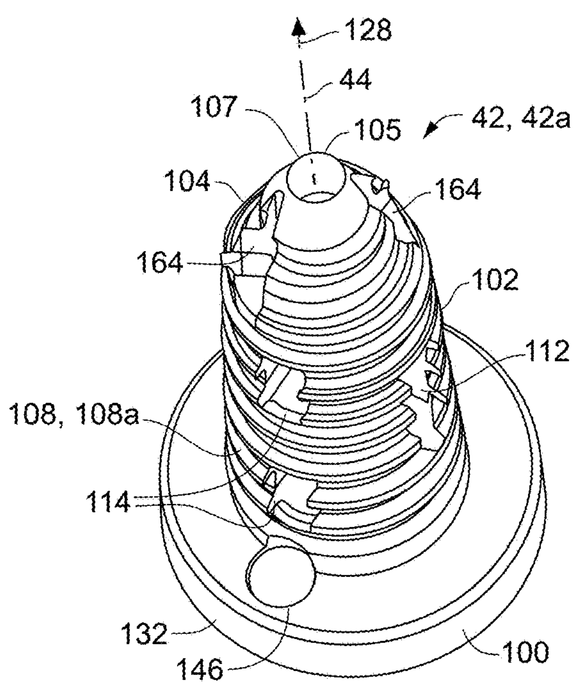
FIG. 3 is a distal perspective view of the primary screw of FIG. 2 according to an embodiment of the disclosure.
Figure 4:
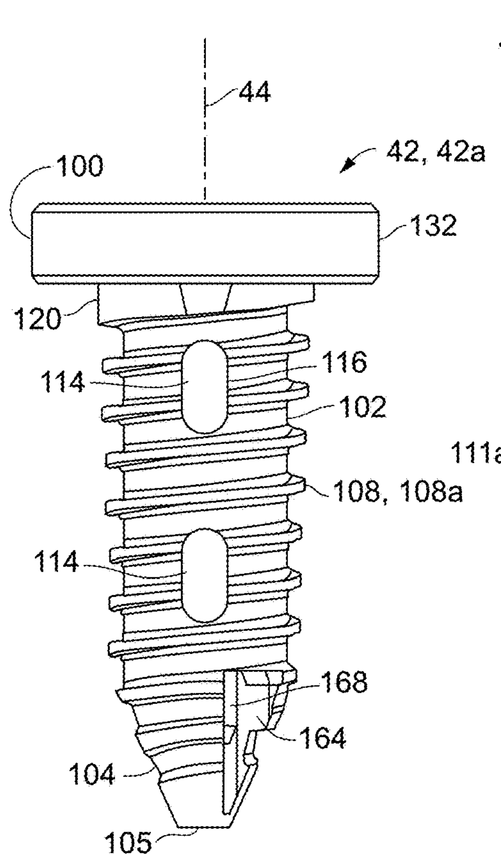
FIG. 4 is a first side elevational view of the primary screw of FIG. 2 according to an embodiment of the disclosure.

Referring to FIG. 1, an implant system 40 for fusion of a sacroiliac joint is depicted according to an embodiment of the disclosure. The implant system 40 includes a main or primary screw 42 that defines a central axis 44 about which the primary screw 42 rotates, the primary screw 42 being configured to detachably mate with an inserter 46. In some embodiments, a main or primary screw driver 48 is configured to access the primary screw 42 through the inserter 46. The primary screw 42, the inserter 46, and the primary screw driver 48 may be configured for sliding over a guide wire or rod 52. The implant system 40 includes a blade assembly 60 including a pair of flexible, elongate blades 62 having proximal ends 64 that are joined to a ring 66. A drive cap 68 may also be included for deployment of the elongate blades 62. The implant system 40 may include one or more side screws 82 for anchoring the primary screw 42, a side screw driver 84 for setting the side screw(s) 82, a plunger assembly 86 for pushing a biologic agent or other grafting material through the primary screw 42, and a multifunctional handle 88 for manipulation of the screw drivers 46 and 84, drive cap 68, and plunger assembly 86. In some embodiments, some or all of the components of the implant system 40 are provided as a kit 90, and may include operating instructions 92 that are provided on a tangible, non-transitory medium. Additional details, functional descriptions, and methods of use for the various components of the implant system 40 are described below.

Figure 5:
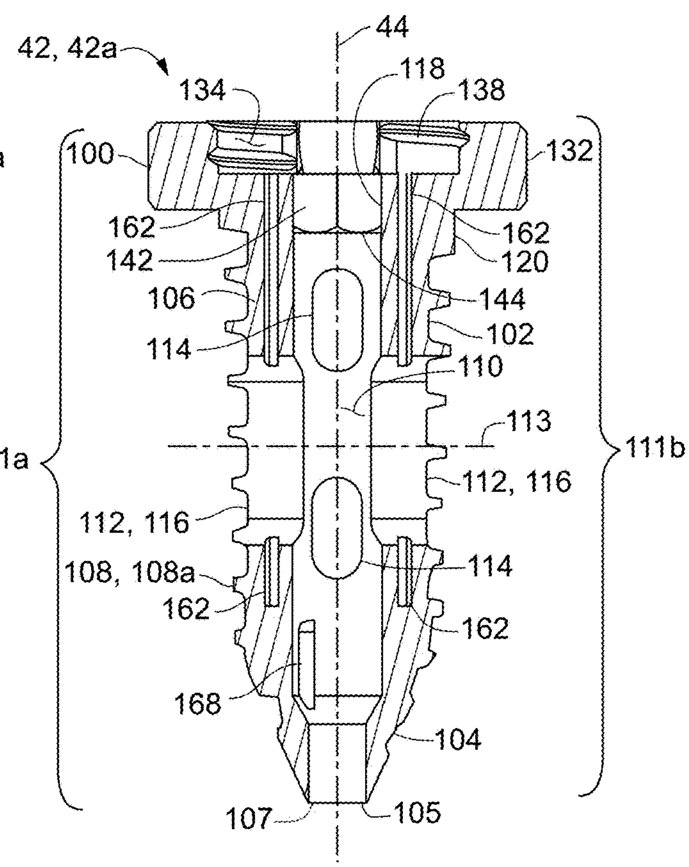
FIG. 5 is a first side sectional view of the primary screw of FIG. 2 according to an embodiment of the disclosure.
Figure 6:
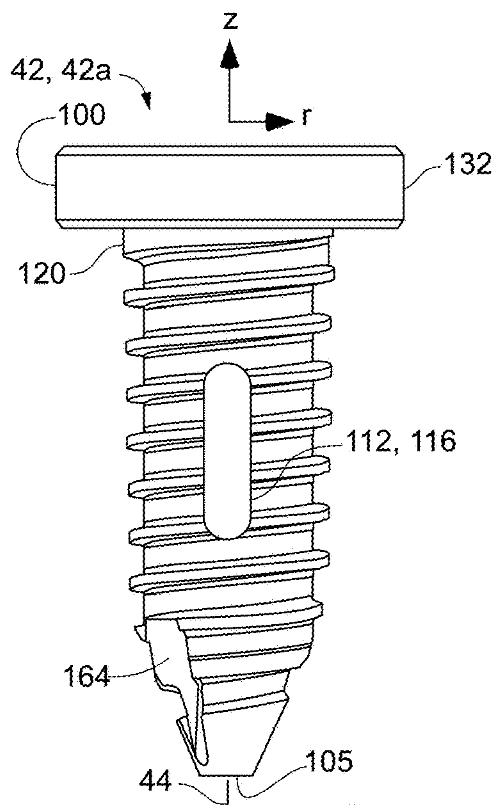
FIG. 6 is a second side elevational view of the primary screw of FIG. 2 according to an embodiment of the disclosure.
Figure 6A:
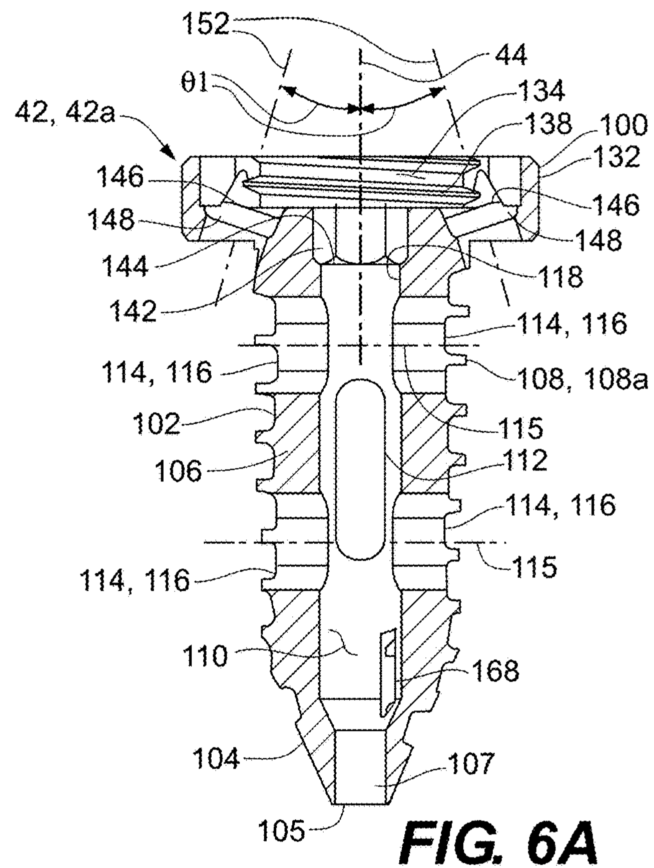
FIG. 6A is a second side sectional view of the primary screw of FIG. 2 according to an embodiment of the disclosure.

Referring to FIGS. 2 through 7, a primary screw 42*a* is depicted according to an embodiment of the disclosure. The primary screw 42*a* includes a head portion 100 and a body portion 102, the body portion 102 including a tip portion 104 having a distal extremity 105 and a side wall 106 concentric about the central axis 44. The side wall 106 defines an opening 107 at the distal extremity 105 for passage of the guide rod 52. The side wall 106 defines external threads 108*a*, an interior chamber 110, and at least one elongate side port 112. In the depicted embodiment, there are two such elongate side ports 112 diametrically opposed and about the central axis 44 on opposing lateral sides 111*a* and 111*b* of the primary screw 42 and centered about a lateral port axis 113 (FIG. 5). Additionally, diametrically opposed side ports 114 may also be defined that extend through the side wall 106, and centered about respective lateral port axes 115 (FIG. 6A). In some embodiments, the lateral port axes 113, 115 intersect and are perpendicular to the central axis 44 of the primary screw. Also, the lateral port axis 113 may be orthogonal to the lateral port axis or axes 115 when viewed along the central axis 44. Each of the side ports 112, 114 are in fluid communication with the interior chamber 110 and defines a respective external opening 116 that faces exterior to the body portion 102 and extends through the external threads 108. The interior chamber 110 is accessible from an opening 118 defined at a proximal end 120 of the body portion 102.

Herein, primary screws, the associated external threads, and the side screw ports 146 are referred to generically or collectively by reference characters 42 and 108, respectively, with specific primary screws 42 and threads 108 being referred to with a letter suffix (e.g., primary screw 42*a* having external threads 108*a*). Also, a "proximal" direction 126 (FIG. 7) of the primary screw 42, as well as the implant system 40 generally, extends parallel to the central axis 44 and toward the operator; a "distal" direction 128 extends opposite the proximal direction 126, i.e., away from the operator.

In some embodiments, the head portion 100 of the primary screw 42 includes a flange 132 that extends radially beyond the side wall 106. The flange 132 and proximal end 120 of the body portion 102 may cooperate to define a recess 134, the flange 132 including one or more inner circular wall portions 136 that bound the recess 134. In the depicted embodiment, two such circular wall portions 136 are depicted. In some embodiments, the inner circular wall portion(s) 136 defines an interior thread 138. In some embodiments, the opening 118 defines a socket 142 at the center and base of the recess 134. The socket 142 may be of any suitable shape for torsional coupling with a tool, such as a polygonal shape (triangle, rectangle, square, hexagon, or octagon—a hexagonal shape being depicted), a cross, or a hexalobular internal drive feature. In some embodiments, the radial dimension of the interior chamber 110 at the proximal end 120 of the body portion 102 and adjacent the socket 142 is smaller than a maximum radial dimension of the socket 142, thus defining a registration surface 144 at the interface of the socket 142 and the interior chamber 110.

In some embodiments, the flange 132 and proximal end 120 of the body portion 102 defines at least one side screw port 146 for receiving one of the side screws 82. Two such side screw ports 146 are depicted. Each side screw port 146 may extend radially beyond the inner circular wall portion(s) 136 and may include a countersink seat 148 for registration of the heads of the side screws 82. Each side screw port 146 extends along a side screw port axis 152 that defines an acute angle θ1 relative to the central axis 44. In some embodiments, the side screw port axes 152 are coplanar.

Herein, primary screws, the associated external threads, and the side screw ports are referred to generically or collectively by reference characters 42, 108, and 146 respectively, with specific primary screws 42, external threads 108, and side screw ports 146 being referred to with a letter or decimal suffix (e.g., primary screw 42*d*; external threads 108*e*; side screw ports 146*g* or 146.1).

The body portion 102 may also defines at least one blade passage 162 that extends axially into the side wall 106, the blade passage(s) 162 being accessible from the proximal end 120 of the body portion 102. There are two such blade passages 162 in the depicted embodiment. In some embodiments, the blade passage(s) 162 extend through the thickness of the elongate side port(s) 112 and terminates distal to the elongate side port(s) 112.

The tip portion 104 may include at least one self-tapping structure 164. The depicted embodiment includes two such self-tapping structures 164. In some embodiments, the self-tapping structure(s) 164 define an aperture 168 that is in fluid communication with the interior chamber 110.

Figure 7:
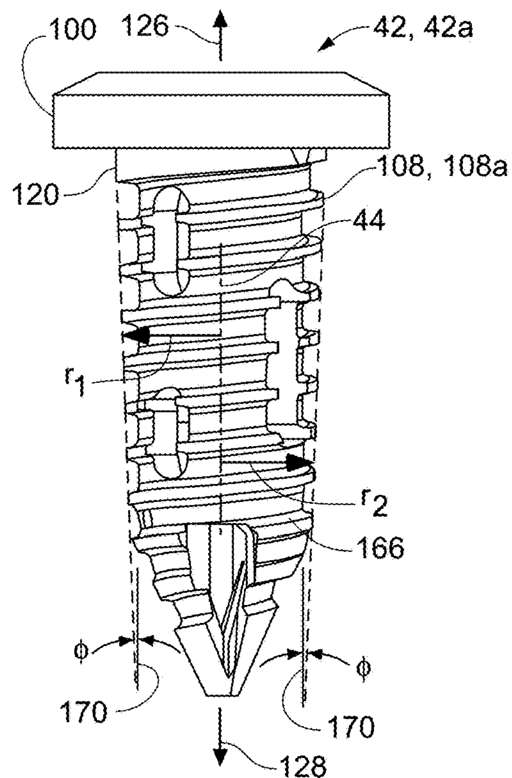
FIG. 7 is an elevational view of the primary screw of FIG. 2 to illustrate a tapered angle of the thread radii according to an embodiment of the disclosure.

The threads 108*a* of the primary screw 42*a* define outer radii that gradually diminish along the body portion 102 in the distal direction 128 (FIG. 7), thereby defining thread radii that are greater near the proximal end 120 than near a tip junction 166 at a base of the tip portion 104. Representative outer radii r1 and r2 relative to the central axis 44 are depicted in FIG. 7, with radius r2 being distal to and less than radius r1. The effect is that the thread radii define a tapered angle ϕ relative to a datum 170 that is parallel to the central axis 44. In the depicted embodiment, the tapered angle ϕ is approximately two degrees. In some embodiments, the tapered angle ϕ is in a range of 0.5 degrees to 5 degrees inclusive. (Herein, a range that is said to be "inclusive" includes the stated endpoints of the range as well as all values between the endpoints.)

Functionally, the greater radii threads 108*a* near the proximal end 120 of the body portion 102 radially penetrate the bone more than the lesser radii threads 108*a* near the tip junction 166 of the body portion 102. Accordingly, the threads 108*a* at the tip junction 166 effectively pre-cut the bone for threads 108*a* at the proximal end 120. The threads 108*a* provide for easier initial setting and overall easier implantation of the primary screw 42*a*, while the larger radii threads 108*a*, by cutting radially deeper into the bone, act to securely fasten the primary screw 42*a*.

Referring to FIGS. 8, 8A, and 8B, a primary screw 42*b* with elongate side ports 112 that are laterally offset is depicted according to an embodiment of the disclosure. The primary screw 42*b* may include many of the same components and attributes as the primary screw 42*a*, which are identified with same numerical references. The elongate side ports 112 are centered about offset lateral axes 172 that are laterally offset relative the central axis 44, such that the offset lateral axes 172 do not intersect the central axis 44. The primary screw 42*b* defines a laterally extending mid-plane 174 that extends parallel to the offset lateral axes 172 and is coplanar with the central axis 44. The elongate side ports include a leading tangential edge 176 and a trailing tangential edge 178. The adjectives "leading" and "trailing" refer to the relative positions of the edges 176 and 178 as the primary screw 42 is rotationally threaded into bone in a cutting rotational direction 109. In some embodiments, the leading tangential edge 176 at the external openings 116 of the elongate side ports 112 are closer to the mid-plane 174 than is the trailing edge 178. The elongate side ports 112 include edge walls 180 that terminate at the external openings 116 of elongate side ports 112. In some embodiments, the edge walls 180 extend parallel to the mid-plane 174 (FIG. 8A). In some embodiments, the portion of the edge wall 180 that terminates at the trailing tangential edge 178 defines an acute sweeping angle γ relative to the mid-plane 174 (FIG. 8B).

Functionally, the leading tangential edge 176 faces toward the bone as the primary screw 42, 42*b* is rotated in the cutting rotational direction 109. As such, the trailing tangential edge 178 may act as a cutting edge that scrapes the bone as the primary screw 42, 42*b* is rotated. By locating the leading tangential edge 176 closer to the mid-plane 174, the trailing tangential edge 178 interfaces with the bone at a more aggressive cutting angle than if the trailing tangential edge 178 were farther from the mid-plane 174, thereby scraping more bone particles which flow into the side ports 112. Embodiments implementing the acute sweeping angle γ at the trailing tangential edge 178 may help sweep the bone particles into the interior chamber 110 of the primary screw 42*b*, thereby mitigating fouling of the side ports 112. The acute sweeping angle γ may also be implemented for side ports 112 that are not offset, for example, the centered side ports 112 of primary screw 42*a*.

Figure 9:
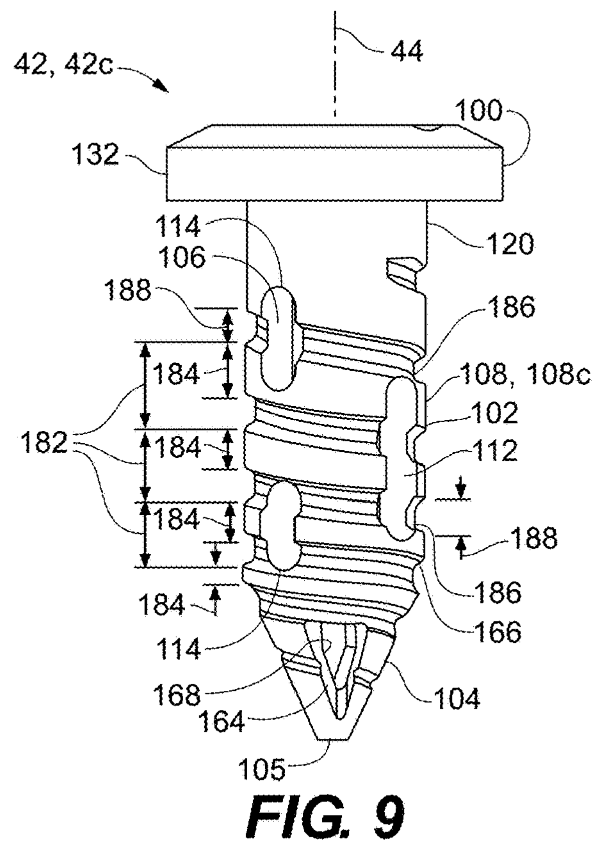
FIG. 9 is an elevational view of a primary screw having threads of varying pitch and crest dimensions along a body portion according to an embodiment of the disclosure.

Referring to FIG. 9, a primary screw 42*c* with an alternative thread configuration 108*c* is depicted according to an embodiment of the disclosure. The primary screw 42*c* may include many of the same components and attributes as the primary screw 42*a*, which are identified with same numerical references in FIG. 9. The thread configuration 108*c* includes both a pitch 182 and a crest 184 that increases along the body portion 102 from the tip junction 166 to the proximal end 120. The thread configuration 108*c* of FIG. 9 is also characterized as having a thread groove 186 having a substantially constant width 188 along the body portion 102. Primary screws 42 with external threads 108 having an increasing pitch but without increasing crest are also contemplated; such an arrangement can be realized by increasing the width of the thread groove. Primary screws 42 with external threads 108 having increasing crest but without increasing pitch are also contemplated; such an arrangement can also be realized by decreasing width of the thread groove.

Functionally, for configurations that utilize the crest 184 that increases from the tip junction 166 to the proximal end 120 of the body portion 102, the crest 184 effectively forms a wedge in spiral form that pushes bone material axially away from the thread and substantially parallel to the edge wall 106 as the primary screw 42 is rotationally threaded into the bone. The bone material is thereby compressed within the thread groove 186, so that the bone material grips and tightens against the threads 108 of the primary screw 42. For configurations that utilize the pitch 182 that increases from the tip junction 166 to the proximal end 120 of the body portion 102, the external threads 108 near the tip junction 166 effectively interfere with the pathway formed by the external threads 108 near the proximal end 120 in a way that imparts a compressive force on the body portion 102. In this way, the bone material is in a tension against the external threads 108 that compresses the body portion 102 to securely hold the primary screw 42 in place. For the depicted primary screw 42*c*, having the threads 108*c* that incorporates both the increasing crest 184 and the increasing pitch 182 from the tip junction 166 to the proximal end 120 of the body portion 102, the combination of the compression of the body portion 102 and the gripping and tightening of the threads 108*c* within the bone may be realized.

Figures 10A, 10B:
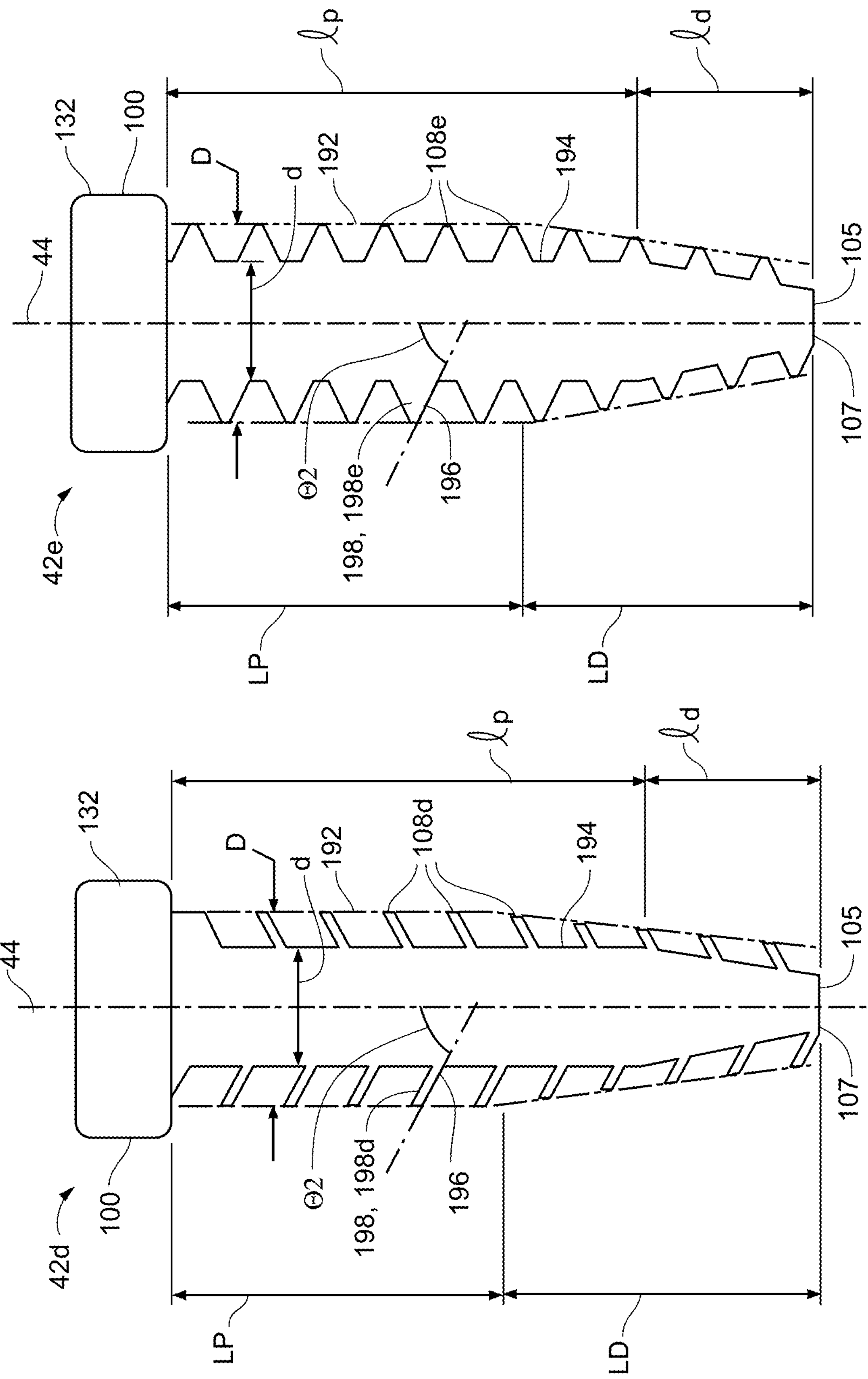
FIGS. 10A and 10B are a schematic sectional views of primary screws having angled threads according to an embodiment of the disclosure.

Referring to FIGS. 10A and 10B, primary screws 42*d* and 42*e* having swept threads 108*d* and 108*e*, respectively, are depicted schematically according to embodiments of the disclosure. The primary screw 42*d* includes many of the same components and attributes as the primary screws 42*a* and 42*c*, some of which are indicated by same-labeled reference characters. The primary screws 42*d* and 42*e* are characterized by threads 108*d* and 108*e* having major diameters D that define a crest profile 192 and minor diameters d that define a root profile 194. In some embodiments, the crest profile 192 is substantially parallel to the central axis 44 along a proximal length LP, and tapers toward the central axis 44 along a tapered distal length LD. Similarly, the root profile 194 may be substantially parallel to the central axis 44 along a proximal length 1*p*, and tapers toward the central axis 44 along a tapered distal length ld. The tapered distal lengths LD and ld extend proximally from the distal extremity 105 of the primary screw 42*d*. In some embodiments, the tapered distal length LD of the crest profile 192 is greater than the tapered distal length ld of the root profile 194. In some embodiments, the tapered distal length LD of the crest profile 192 is in a range 7 millimeters to 13 millimeters inclusive. In some embodiments, the tapered distal length ld of the root profile 192 is in a range 3 millimeters to 7 millimeters inclusive.

In some embodiments, the threads 108*d*, 108*e* are inclined distally or "swept back", so that a distal face 196 the flanks 198 of the threads 108*d* define an acute swept angle θ2 relative central axis 44. In some embodiments, the acute swept angle θ2 is within a range of 60 degrees to 80 degrees inclusive. In some embodiments, the acute swept angle θ2 is within a range of 75 degrees to 80 degrees inclusive. The flanks 198 of the threads 108*d* may define a cantilever profile 198*c* that is canted at the acute swept angle θ2 (FIG. 10A). In other embodiments, the flanks 198 of the threads 108*d* may define a triangular- or frustum-shaped profile 198*d* (FIG. 10B).

Functionally, the shorter tapered distal length ld of the root profile 194 relative to the tapered distal length LD of the crest profile 192 promotes pushing of soft tissue such as flesh and muscle radially away from an access approach rather than cutting or tearing the soft tissue. By favoring pushing the soft tissue aside over tearing or cutting, the soft tissue may heal faster. The swept threads 108*d* also favors the radial displacement of soft tissue instead of cutting or tearing of the tissue. In some embodiments, the displacement of soft tissue eliminates the need for a dilator during the surgical process.

Figures 11, 12A, 12B:
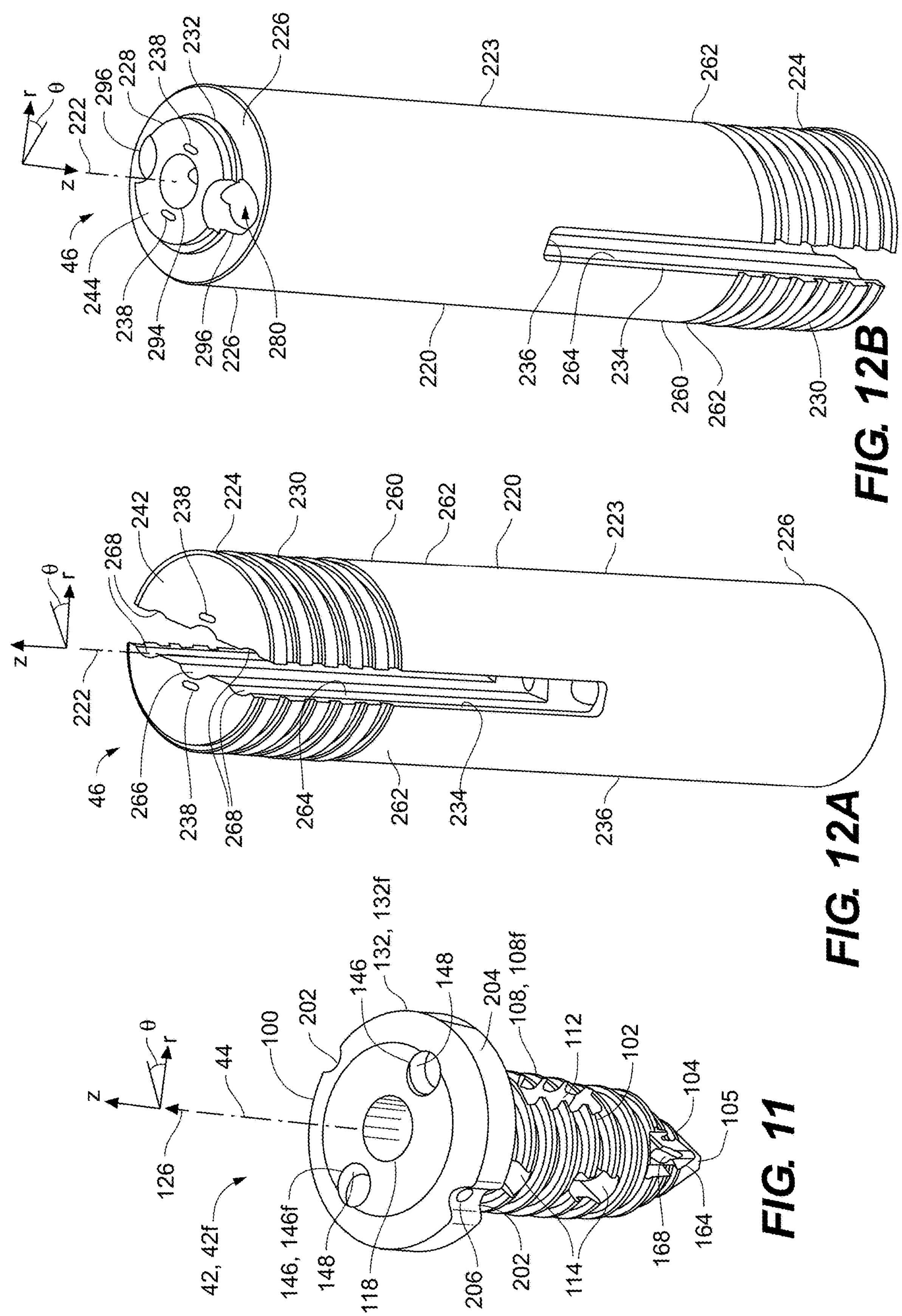
FIG. 11 is a proximal perspective view of a primary screw having a flange with external notches according to an embodiment of the disclosure.
FIG. 12A is a proximal perspective view of an inserter according to an embodiment of the disclosure.
FIG. 12B is a distal perspective view of the inserter of FIG. 12A according to an embodiment of the disclosure.

Referring to FIG. 11, a primary screw 42*f* with a flange 132*c* is depicted according to an embodiment of the disclosure. The primary screw 42*f* may include many of the same components and attributes as the primary screws 42*a* and 42*c*, some of which are indicated by same-labeled reference characters. The flange 132*c* is configured for coupling to a tool (not depicted) with notches 202 on a radial outward face 204 thereof. Accordingly, in some embodiments, the head portion 100 need not define the recess 134 of primary screws 42*a* or 42*c*. In FIG. 11, there are a pair of diametrically opposed notches 202 rotationally offset from the side screw ports 146. Additional notches are also contemplated, for example three notches spaced at 120 degrees apart or four notches spaced at 90 degrees apart. The flange 132*c* may include radially extending apertures 206 disposed radially inward at the notches 202.

Functionally, the notches 202 provide an interface for gripping the primary screw 42*f* with a tool. The apertures 206 may also be part of the tool interface, for alignment, structural enhancement, or both. The tool may be stout enough to enable driving of the primary screw 42*f* into bone using just the notches 202 or the notches 202 and apertures 206 in combination, so that no additional driving feature, such as the socket 142 of primary screw 42*a* or 42*c*, is needed. Alternatively, the tool may be an inserter similar to inserter 46 modified to couple with the notches 202, not designed to drive the primary screw 42*f* but through which driving tools access the primary screw 42*f*; in such an arrangement, the head portion 100 may define, for example, structure similar to the socket 142 (not depicted in FIG. 11) for coupling with the driving tools.

Referring to FIGS. 12A through 22, the inserter 46 is depicted according to an embodiment of the disclosure. The inserter 46 includes a main cylinder 220 concentric about an inserter axis 222 and having an exterior surface 223, a proximal end 224 and a distal end 226, with a boss 228 extending from the distal end 226. The main cylinder 220 may include external threads 230 formed at the proximal end 224. The boss 228 may include an exterior thread 232 configured to threadably engage the interior thread 138 of the inner circular wall portion(s) 136 of the recess of the primary screw 42*a* or 42*c*. In some embodiments, an access slot 234 extends axially from the proximal end 224 of the main cylinder 220, a distal end 236 of the access slot 234 extending to a mid-portion of the main cylinder 220 and passing laterally through the main cylinder 220. The main cylinder defines at least one blade passage 238 that extends axially and parallel to the inserter axis 222, each blade passage 238 passing through a proximal face 242 of the main cylinder 220 and a distal face 244 of the boss 228.

In some embodiments, the access slot 234 bifurcates a proximal portion 260 of the main cylinder 220 into two opposed arcuate wall portions 262, each including an inner surface 264. Each inner surface 264 defines a central arcuate channel 266 and at least one side arcuate channel 268. The arcuate channels 266 and 268 extend parallel to the inserter axis 222. The central arcuate channels 266 of the opposed inner surfaces 264 are mirrored about the access slot 234 and concentric about the inserter axis 222. The at least one side arcuate channel 268 of the opposed inner surfaces 264 are mirrored about the access slot 234. In the depicted embodiment, each inner surface 264 defines two such side arcuate channels 268 that are on laterally opposing sides of the central arcuate channel 266.

The main cylinder 220 defines an interior chamber 280 having an interior wall 282. In some embodiments, the interior chamber includes a main or central chamber 284 and at least one antechamber 286 that are in fluid communication. In the depicted embodiment, there are two antechambers 286, each coplanar with and distal to the access slot 234. Each antechamber 286 intersects with the central chamber 284, defining a passageway 288 therebetween. The main cylinder 220 defines a central entrance port 290 and at least one side entrance port 292 that are in fluid communication with the interior chamber 280. In the depicted embodiment, the central port 290 is concentric with the inserter axis 222 and provides access to the central chamber 284, and there are two side entrance ports 292, each being defined at the junction of the access slot 234 and a respective one of the antechambers 286. The entrance ports 290, 292 are internal to the main cylinder 220 and located proximate the distal end 236 of the access slot 234.

The main cylinder 220 also defines a central egress port 294 and at least one side egress port 296 that are in fluid communication with the interior chamber 280. The egress ports 294, 296 pass through the distal end 226 of the main cylinder 220 and the boss 228. Each side entrance port 292 and side egress port 296 combines with the interior chamber 280 to define a cross passage 297 that extends along a respective canted axis 298. In some embodiments, each canted axis 298 crosses the inserter axis 222 and defines the acute angle θ1 relative to the inserter axis 222. In the depicted embodiment, the central egress port 294 is concentric about the inserter axis 222 at the distal end of the central chamber 284. As there are two side entrance ports 292 in the depicted embodiment, there are also cross passages 297 and two side egress ports 296 aligned along two canted axes 298. In the depicted embodiment, the canted axes 298 are coplanar with a central plane of the access slot 234.

The interior wall 282 defines at least one guide ramp 299 that extends radially inward, one for each side entrance port 292. Each guide ramp 299 is centered distal to the corresponding side entrance port 292 and extends adjacent the corresponding canted axis 298. The depicted embodiment, having two side entrance ports 292, also has two guide ramps 299. Also in the depicted embodiment, the guide rams 299 are disposed in the antechambers 286.

Figures 40, 41:
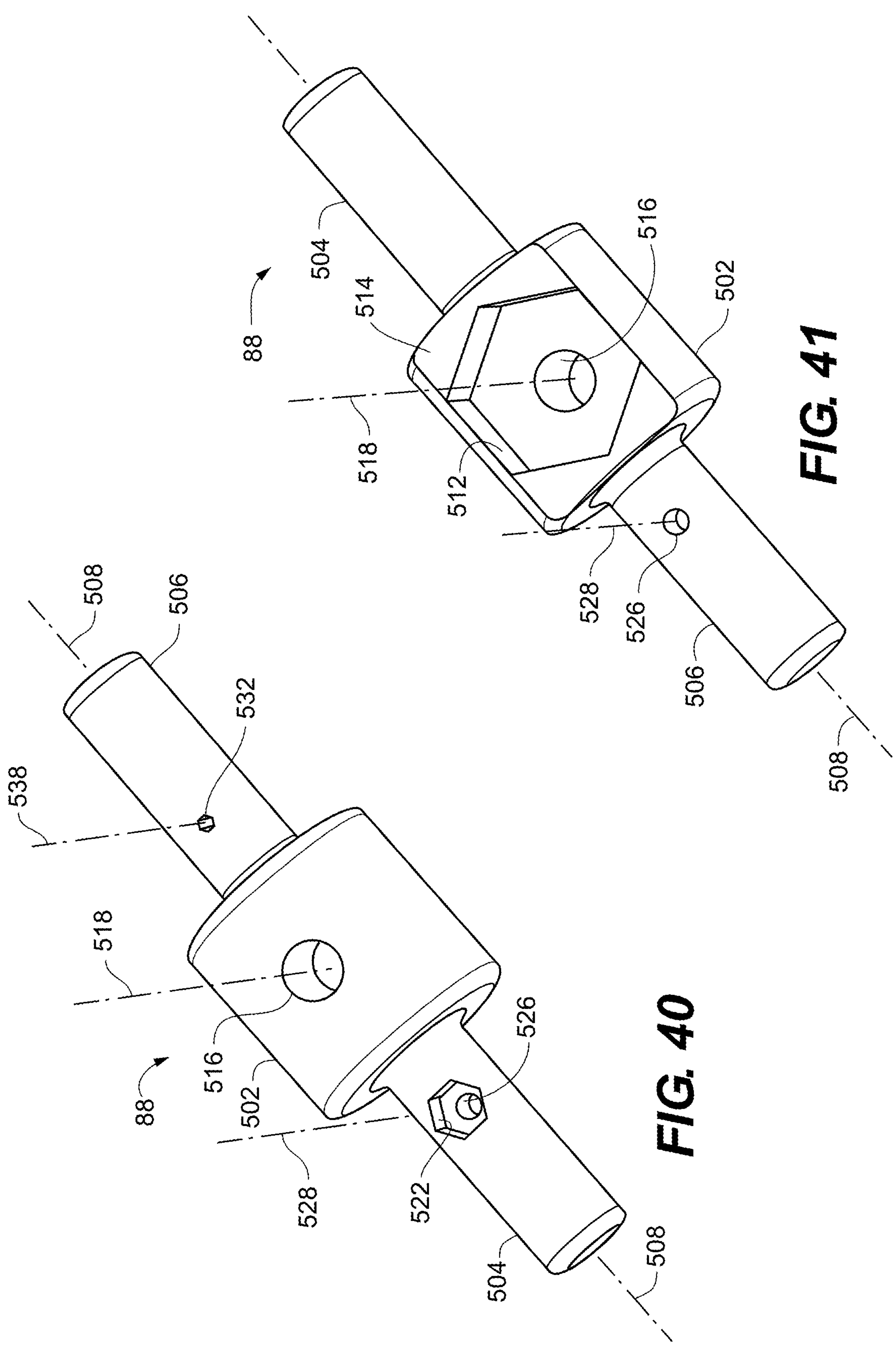
FIG. 40 is an enlarged perspective view of a first side of a multifunctional handle according to an embodiment of the disclosure.
FIG. 41 is an enlarged perspective view of a second side of the multifunctional handle of FIG. 40 according to an embodiment of the disclosure.

Referring to FIGS. 22 and 23, the guide rod 52 is described in further detail according to an embodiment of the disclosure. The guide rod 52 includes a shaft portion 302 having proximal end 304 and a distal end 306. The distal end 306 may include a self-tapping threaded structure 308 at a distal extremity 312. In some embodiments, flats 314 are formed adjacent the threaded structure 308 at the distal end 306, forming a driving head 316 defining a polygonal cross section that is shaped and dimensioned to mate with a socket 420 (FIG. 29) of the side screw(s) 82. In some embodiments, the driving head 316 is dimensioned to form a press fit with the socket 420, to provide a stable coupling between the driving head 316 and the side screw 82. Flats 318 may also be formed at the proximal end 304, for mating with a socket 532 on the multifunctional handle 88 (FIG. 40).

Functionally, the self-tapping threaded structure 308 enables the guide rod 52 to be readily anchored at a penetration site where the primary screw 42 is to be implanted. In some embodiments, the flats 314 at the distal end 306, being configured to mate with the socket 420 of the side screw(s) 82, enable the guide rod 52 to also serve as a driver for the side screw(s) 82. Of course, the sockets 420 of such side screws require sufficient depth to accommodate the threaded structure 308 when the distal end 306 is inserted into the socket 420. The flats 318 at the proximal end 304 enable torsional driving of the guide rod 52, be it for anchoring the threaded structure 308 into bone or for driving the side screws 82.

Referring to FIG. 24, the primary screw driver 48 is described in more detail according to an embodiment of the disclosure. The primary screw driver 48 includes a shaft portion 320 defining a central passage 322 concentric about a central axis 324. The central passage 322 passes through the entire length of the shaft portion 320, from a proximal end 326 and a distal end 328.

The proximal end includes wrench flats 330 formed thereon. In some embodiments, the wrench flats 330 extend radially beyond a nominal radius 332 of a main body 334 of the shaft portion 320 (depicted). Alternatively, the wrench flats 330 may be radially inset from the main body 334. The wrench flats 330 may define a polygonal shape, such as a triangle, square, hexagon (depicted), or octagon. The distal end 328 includes a driving head 336 shaped for mating with the socket 142 of the primary screw 42. The driving head 336 may be radially inset from the nominal radius 332 of the main body 334 of the shaft portion 320. The main body 334 may also define one or more lateral through-holes 338 that are in fluid communication with the central passage 322. In the depicted embodiment, there are four such lateral through-holes 338 located near the distal end 328, the through-holes 338 being axially elongate and uniformly distributed about the central axis 324.

In some embodiments, the primary screw driver 48 includes a ring guide 342 for alignment and rotational coupling with the ring 66 of the blade assembly 60. The ring guide 342 may include a pad or rail 344 mounted to or formed on the main body 334 of the shaft portion 320 that extends beyond the nominal radius 332 of the main body 334 of the shaft portion 320. In the depicted embodiment, there are two such rails 344, diametrically opposed and extending axially along the main body 334 near the proximal end 326. More or less than two rails 344 are contemplated. Alternatively, the ring guide 342 may be of other forms, including flats or grooves that extend distally from the proximal end 326 of the screw driver 48 and are inset from the nominal radius 332 of the main body 334 of the shaft portion 320.

Figures 25, 26, 27:
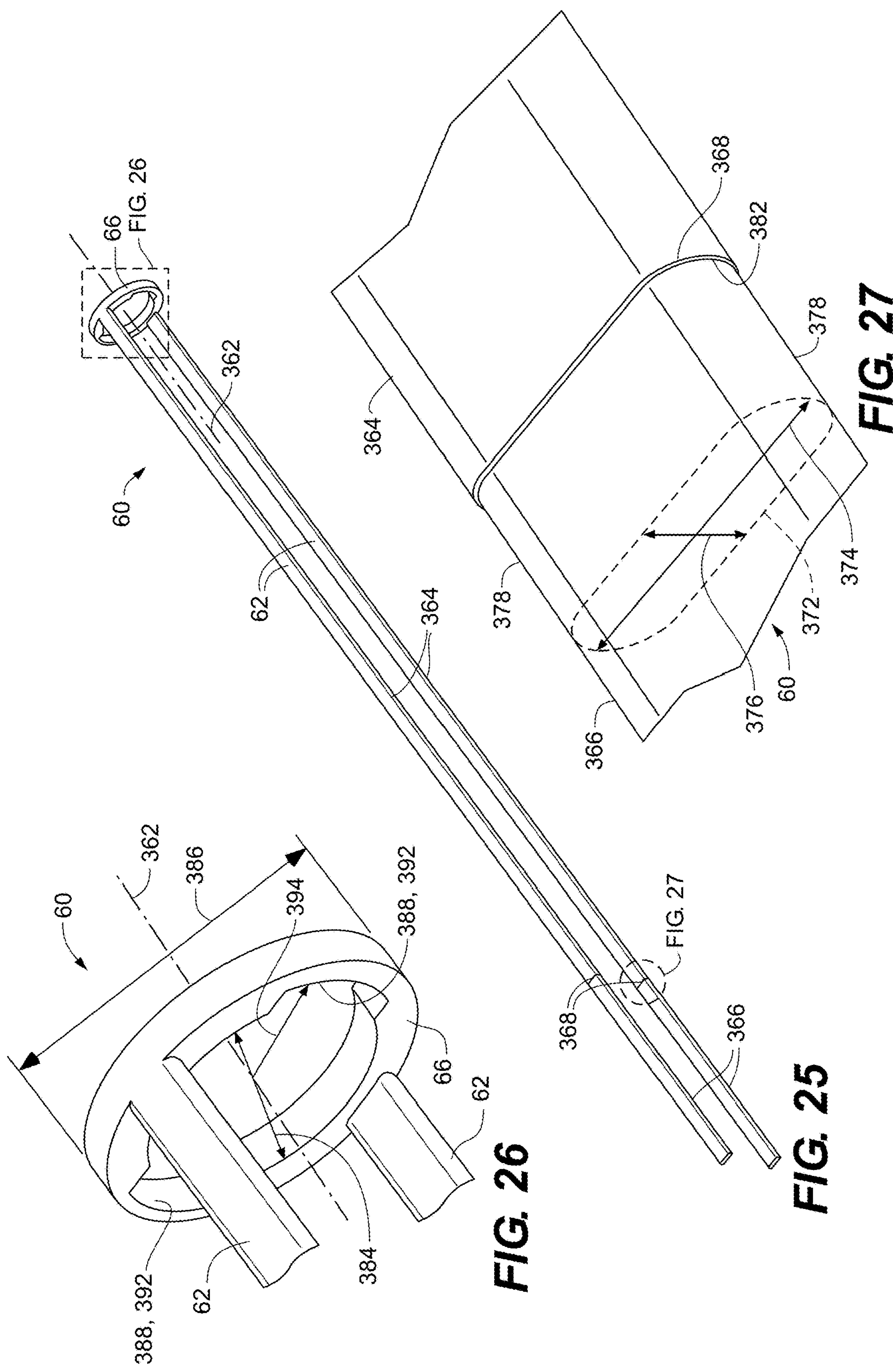
FIG. 25 is a perspective view of a blade assembly of FIG. 1 in isolation.
FIG. 26 is an enlarged partial view of the proximal end of the blade assembly of FIG. 25 according to an embodiment of the disclosure.
FIG. 27 is an enlarged partial view of a transition between a proximal portion and a distal portion of a blade of the proximal end of the blade assembly of FIG. 25 according to an embodiment of the disclosure.

Referring to FIGS. 25 through 27, the blade assembly 60 is described in more detail according to an embodiment of the disclosure. In some embodiments, the blade assembly 60 is axisymmetric about a ring axis 362 that is concentric with the ring 66. In some embodiments, each flexible, elongate blade 62 includes a proximal portion 364 and a distal portion 366 that transition together at a junction 368. In some embodiments, the distal portion 366 defines an oblong cross-section 372 having a major dimension 374 and a minor dimension 376, the major dimension 374 extending tangential to the ring axis 362 and the minor dimension 376 extending substantially radially relative to the ring axis 362. The distal portion 366 defines edges 378 at the extremities of the major dimension 374. The edges 378 may be of any appropriate geometry for tissue cutting, including a radiused edge (depicted), a centered ridge, or an offset ridge.

The proximal portion 364 is of greater dimensions than the distal portion 366. In the depicted embodiment, the proximal portion 364 defines a similarly shaped but enlarged cross-section. Other cross-sections may be utilized for the proximal portion 364, including a square, rectangular, circular, or elliptical cross-section. The junction 368 may define a step transition 382 (depicted) or a tapered transition.

The ring 66 defines an inner radius 384 and an outer radius 386, and includes features 388 for sliding engagement with the ring guide 342. In some embodiments, the features 388 include at least one keyway 392 defined in the ring 66, the keyway 392 extending radially outward from the inner radius 384 to define a maximum inner radius 394 of the ring 66. For the depicted embodiment, there are two such keyways 392, each sized and shaped to slide over the rails 344 of the primary screw driver 48.

Functionally, the larger cross-section of the proximal portion 364 provides stoutness to prevent buckling of the proximal portion 364 when the distal portion 366 of the blades 62 are axially compressed to flex the distal portion 366. The oblong cross-section 372 of the distal portion 366, having the major dimension 374 extending tangentially, provides stiffness in the tangential direction so that the distal portion 366 of the blade 62 flexes in the radial direction.

Figure 29:
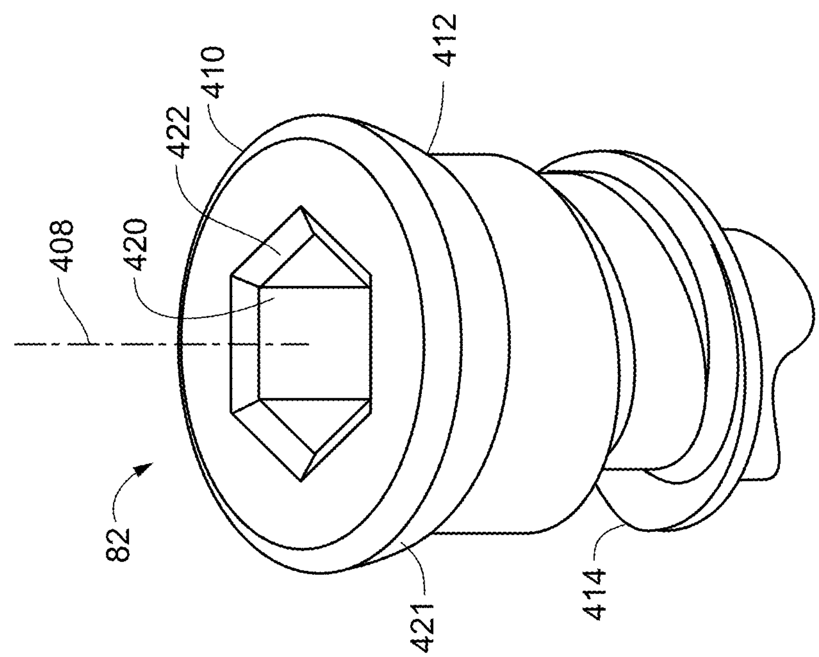
FIG. 29 is a partial, enlarged view of a proximal end of the side screw of FIG. 28 according to an embodiment of the disclosure.
Figure 28:
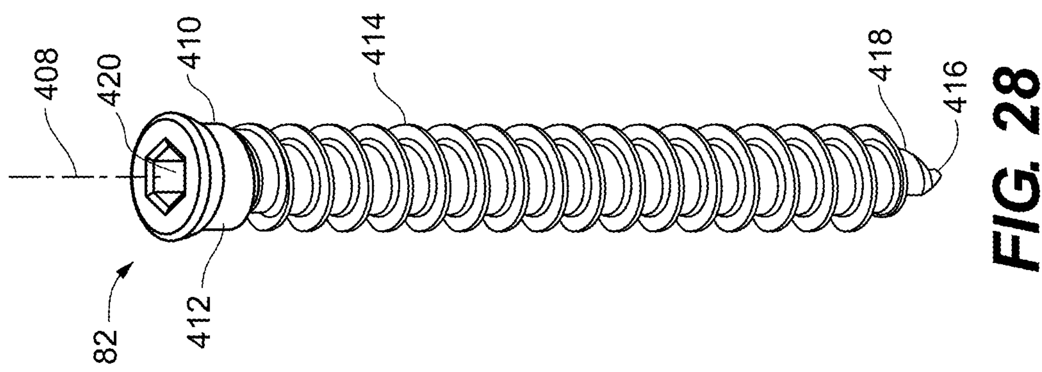
FIG. 28 is an enlarged perspective view of a side screw of FIG. 1 in isolation.

Referring to FIGS. 28 and 29, the side screw(s) 82 are described in further detail according to an embodiment of the disclosure. Each side screw 82 defines a side screw axis 408 and includes a head 410 at a proximal end 412 thereof, from which a threaded shaft 414 depends. The threaded shaft 414 may converge to a point 416 at a distal end 418. In some embodiments, the side screws are self-tapping (not depicted). The head 410 defines a socket 420 and may include a flange 421 that extends radially beyond the threaded shaft 414. In some embodiments, the socket 420 includes a chamfered lead-in 422. The socket 416 may define any one of a variety of shapes, such as a triangle, rectangle, square, hexagon (depicted), octagon, cross, hexalobular internal drive feature, or other shapes suitable for torsional driving of the side screw 82.

Figure 30:
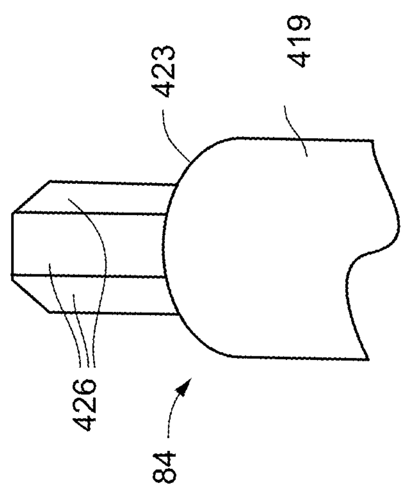
FIG. 30 is an enlarged, partial perspective view of a proximal end of a side screw driver of FIG. 1 according to an embodiment of the disclosure.
Figure 31:
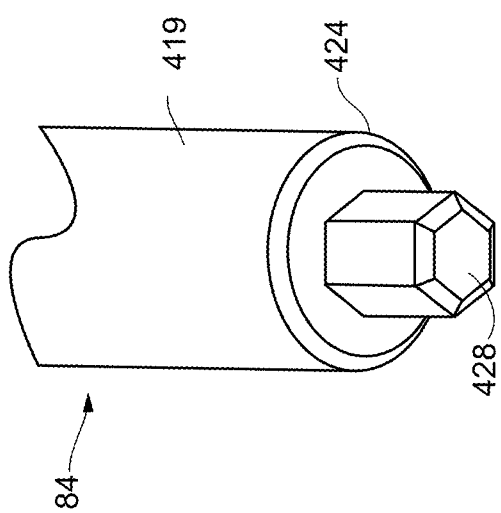
FIG. 31 is an enlarged, partial perspective view of a distal end of a side screw driver of FIG. 1 according to an embodiment of the disclosure.

Referring to FIGS. 30 and 31, the optional side screw driver 84 is described in further detail according to an embodiment of the disclosure. The side screw driver 84 includes a shaft 419 proximal end 423 and distal end 424. The proximal end 423 may include flats 426 for application of a wrench (e.g., multifunctional handle 88) for torqueing the side screw driver 84. In some embodiments, the flats 426 define a polygonal cross-section (hexagonal depicted). The distal end 424 may include a driving head 428. The driving head 424 is configured to mate with the socket 420 of the side screw(s) 82. Accordingly, for the depicted embodiment, the driving head 428 of the side screw driver 84 is hexagonal. Like the driving head 316 of the guide rod 52, the driving head 428 may be dimensioned to form a press fit with the socket 420, to provide a stable coupling between the driving head 428 and the socket 420 while guiding the side screw 82 through the inserter 46 (described below).

Figure 32:
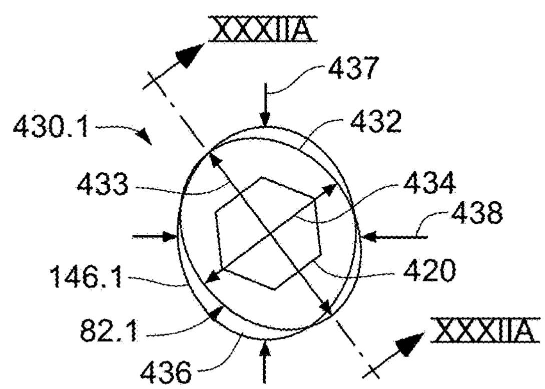
FIG. 32 is an end view of a side screw with an oblong head initially contacting an oblong side screw port of a primary screw according to an embodiment of the disclosure.
Figure 33:
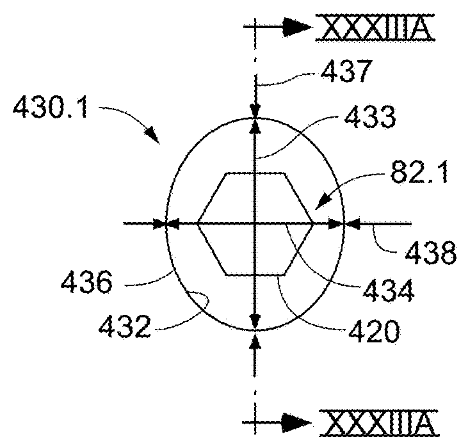
FIG. 33 is an end view of the side screw and side screw port of FIG. 32 with the side screw fully seated within the side screw port according to an embodiment of the disclosure.
Figure 33A:
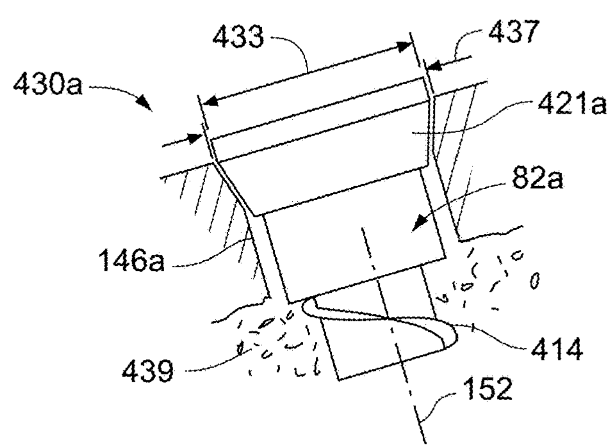
FIG. 33A is a partial sectional view of the side screw and side screw port along plane XXXIIIA-XXXIIIA of FIG. 33 according to an embodiment of the disclosure.

Referring to FIGS. 32 through 33A, a locking configuration 430.1 for a side screw 82.1 is depicted according to an embodiment of the disclosure. In this embodiment, a flange 421.1 of the side screw 82.1 defines an oblong or elliptical shape 432 characterized by a major dimension 433 and a minor dimension 434. Side screw ports 146.1 of the primary screw 42 may also define an oblong or elliptical shape 436 characterized by a major dimension 437 and a minor dimension 438. The oblong shape 436 of side screw ports 146.1 are dimensioned to fully receive and mate with the oblong shape 432 of the flange 421.1 when the major axes 433 and 437 are aligned, as in FIG. 33.

Figure 32A:
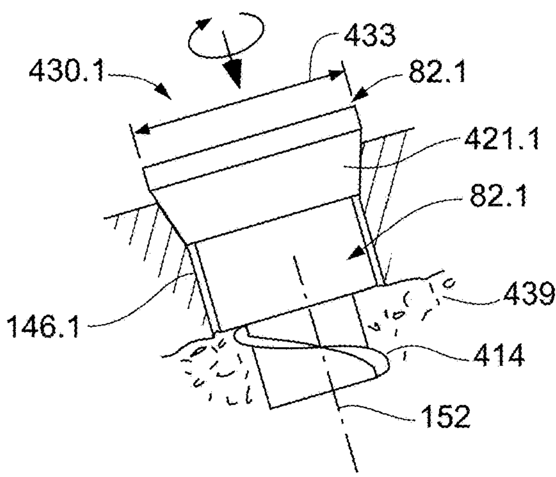
FIG. 32A is a partial sectional view of the side screw and side screw port along plane XXXIIA-XXXIIA of FIG. 32 according to an embodiment of the disclosure.

In operation, the side screw 82.1 is screwed into a bone 439 and the flange 421.1 brought into initial contact with the edges of the side screw port 146.1. For this initial contact, the respective major axes 433 and 437 of the oblong shapes 432 and 436 are not aligned (FIG. 32) and the side screw 82.1 is not fully set within the screw port 146.1 (FIG. 32A). The surgeon continues to drive the screw 82.1 into the bone 439, causing the major dimension 433 of the flange 421.1 to rotate toward alignment with the major dimension 437 of the side screw port 146.1, and also causing the side screw 82.1 to be drawn against and into the side screw port 146.1. The side screw 82.1 is thus driven into the bone 439 until the major axes 433 and 437 are aligned and the flange 421.1 is seated within the side screw port 146.1 (FIGS. 33 and 33A). The mating of the oblong shapes 432 and 436 resists rotation of the side screws 82.1, thereby locking the side screws 82.1 in place and inhibiting the side screws 82.1 from rotating after implantation and backing out of the side screw sockets 146.1.

Figure 34A:
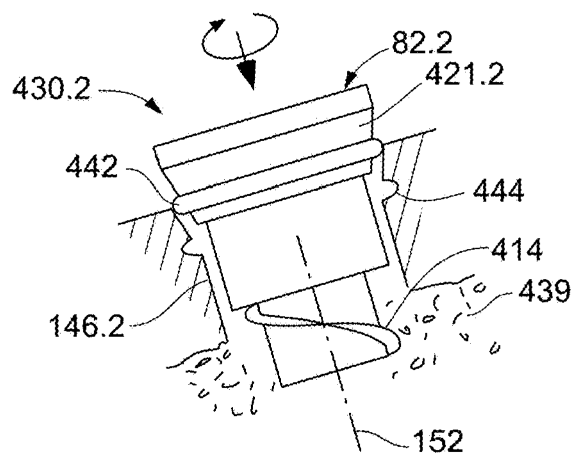
FIG. 34A is a partial sectional view of a side screw with a detent initially contacting a side screw port with a groove for receiving the detent according to an embodiment of the disclosure.
Figure 34B:
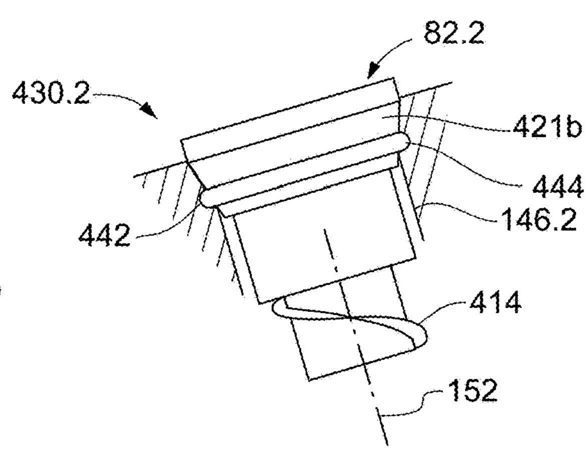
FIG. 34B is a partial sectional view of the side screw fully seated within the side screw port of FIG. 34A according to an embodiment of the disclosure.
Figure 35A:
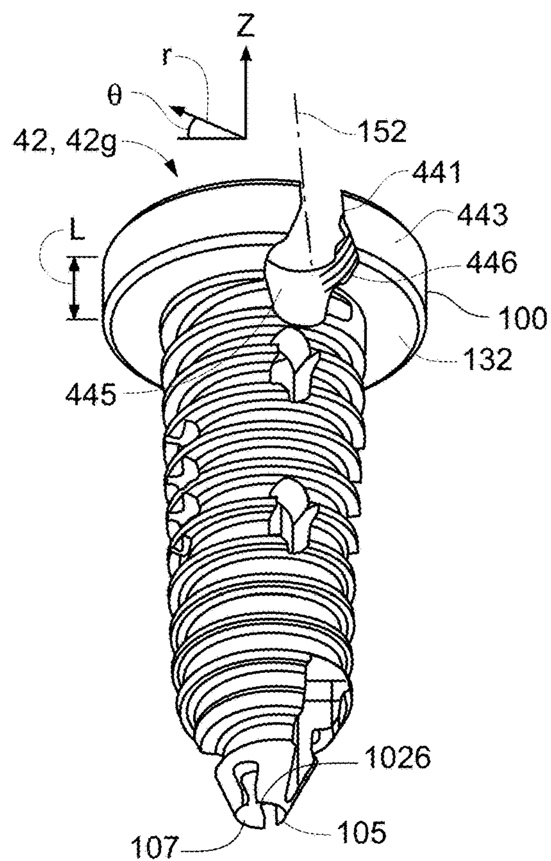
FIG. 35A is a lower perspective view of a primary screw having a breach in the flange according to an embodiment of the disclosure.
Figure 35B:
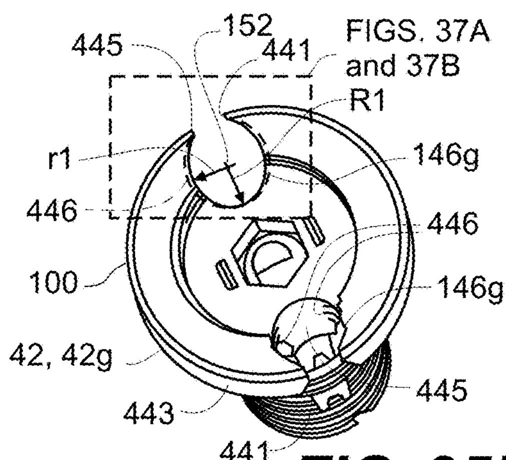
FIG. 35B is an upper perspective view of the primary screw of FIG. 35A as viewed along a side screw port axis according to an embodiment of the disclosure.

Referring to FIGS. 34A and 34B, a second locking configuration 430.2 for a side screw 82.2 is depicted according to an embodiment of the disclosure. In this embodiment, a flange 421.2 of the side screw 82.2 includes a detent ring 442, and a side screw port 146.2 includes a complementary groove 444 configured to receive the detent ring 442. The detent ring 442 projects radially outward from the contour of the flange 421.2. Alternatively, the screw port may define the detent, and the flange may define the complementary groove (not depicted).

In operation, the side screw 82.2 is screwed into the bone 439 and the detent ring 442 brought into initial contact with the side screw port 146.2 (FIG. 34A). For this initial contact, the detent ring 442 is not disposed within the groove 444. The surgeon continues to drive the screw 82.2 into the bone 439, causing the detent ring 442 to be drawn against the side screw port 146.2 and toward the groove 444 until the detent ring 442 snaps into the groove 444 (FIG. 34B). The mating of the detent ring 442 and groove 444 prevents the side screws 82.2 from backing out of the side screw ports 146.2.

The side screws 82.1, 82.2 and side ports 146.1, 146.2, have many of the same components and attributes as the side screws 82 and side screw ports 146, some of which are indicated in FIGS. 32 through 33A by same-labeled reference characters. It is understood that discussion herein pertaining to the side screws 82 and side screw ports 146 apply generally to embodiments utilizing the side screws 82.1, 82.2 and the side ports 146.1, 146.2.

Referring to FIGS. 35A through 37B, a third locking configuration 430.3 and components thereof is depicted according to an embodiment of the disclosure. A side screw 82.3 and a primary screw **42*g* of the third locking configuration 430.3 may include many of the same components and attributes as the side screws 82 and primary screws 42 generally, some of which are indicated by same-labeled reference characters. For the third locking configuration 430*c*, the primary screw 42*g* may be configured so that side screw ports 146*g* define a breach or gap 441 that extends an axial length L of an outer diameter surface 443 of the flange 132, so that the side screw ports 146*g* do not form a closed diameter hole. Rather, the side screw ports 146*g* may instead define what may be characterized as a "C-shape" when viewed along the respective side screw port axis 152 (FIG. 35B). In some embodiments, the side screw port 146*g* defines an oblong through hole having a major radius R1 and a minor radius r1 about the side screw port axis 152. In some embodiments, a socket wall 445 of each side screw port 146*g* defines female threads 446 having a constant radius (circular) root diameter about the side screw port axis 152**, the root diameter defining a maximum radius R.

Figure 36:
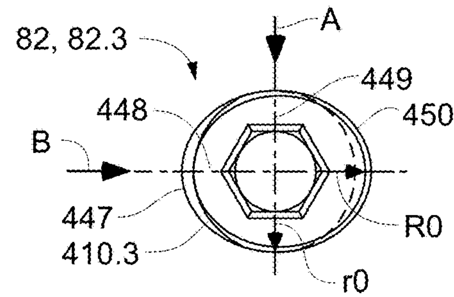
FIG. 36 is a top view of a side screw according to an embodiment of the disclosure.
Figure 36A:
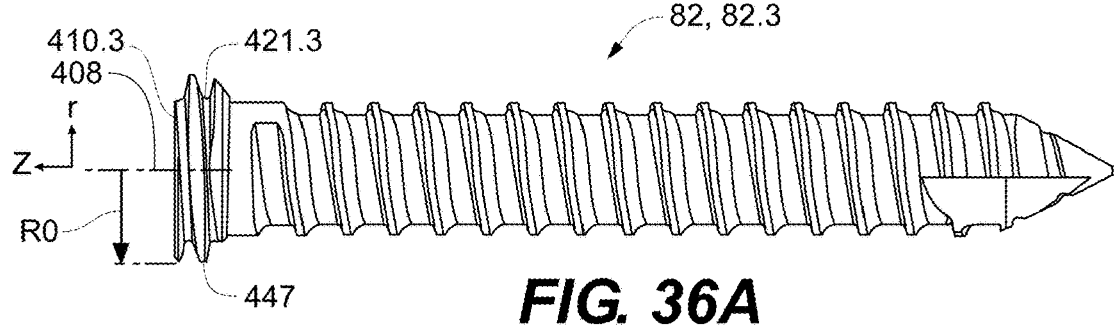
FIG. 36A is a side view from a perspective A of FIG. 36 according to an embodiment of the disclosure.
Figure 36B:
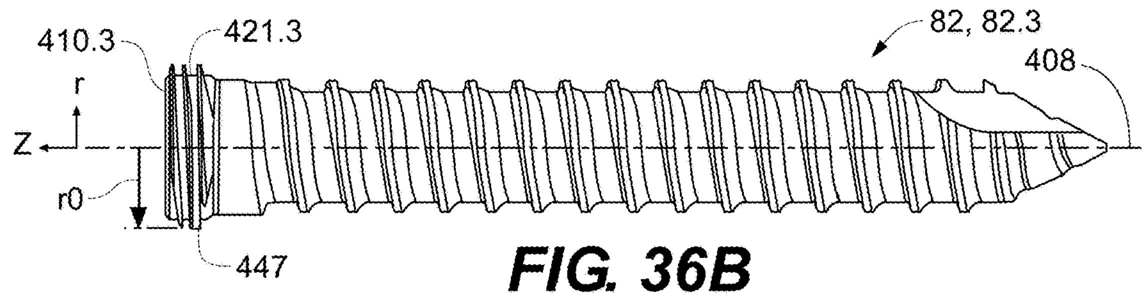
FIG. 36B is a side view from a perspective B of FIG. 36 according to an embodiment of the disclosure.

The side screw 82.3 defines a head 410.3 having oblong threads 447. The oblong threads 447 extend radially from a flange 421.3 of the head 410.3 along a major axis 448 to define a major radius R0 (FIGS. 36, 36A). The radial dimension of the oblong threads 447 taper off in the tangential direction to define a minor axis 449 that is orthogonal to the major axis 448, the oblong threads 447 defining a minor radius r0 along the minor axis 449 (FIGS. 36, 36A). The oblong threads 447 thereby define an oblong profile 450 of the side screw 82.3 when viewed from the top end (FIG. 36), wherein the threads at the major radius R0 have a substantially greater radial engagement depth with the female threads 446 than do the threads at the minor radius.

In some embodiments, the female threads 446 are circular about the side screw port axis 152. Because the radius of the circular female threads 446 are less than the major radius R1 of the side screw port 146*g* but greater than the minor radius r1 of the side screw port 146*g*, the circular female threads 446 may cut into only a portion of the socket wall 445 centered about the minor radius r1 (depicted). In some embodiments, the pitch of the threads 446 and 447 are the same pitch as the threads of the side screw 82.3.

Figure 37A:
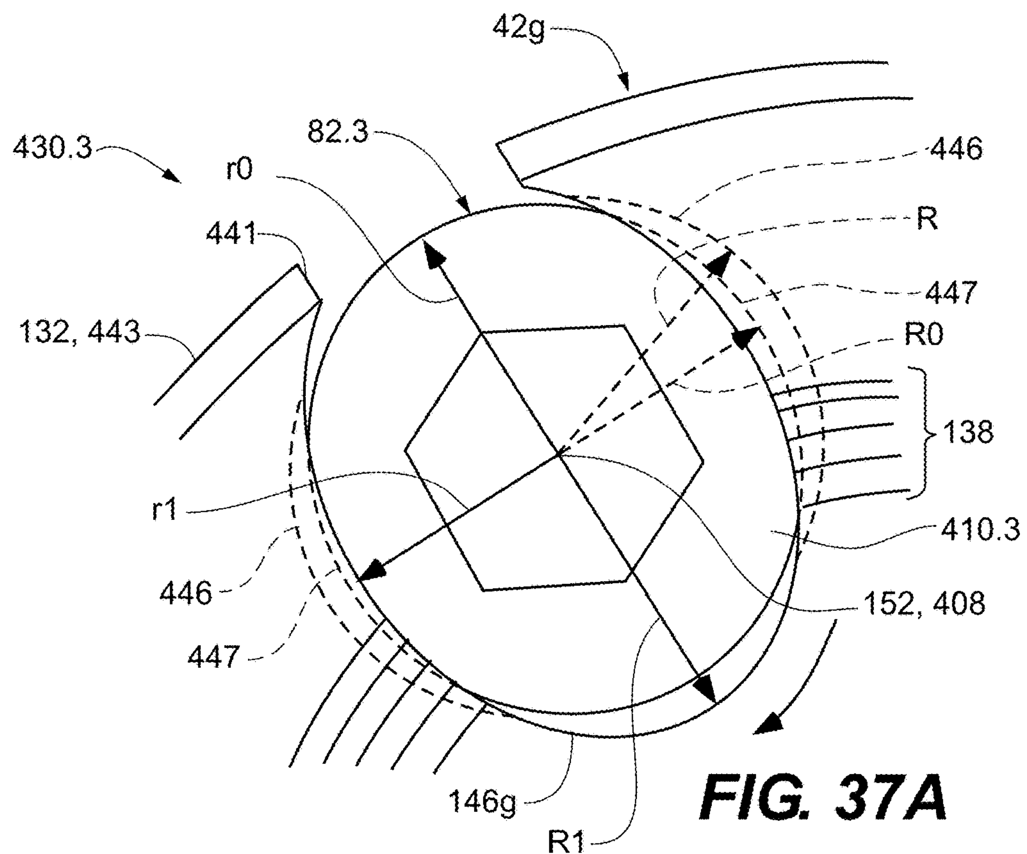
FIG. 37A is an enlarged, partial perspective view of FIG. 35B with the side screw of FIG. 36 disposed within a side screw port and having a major dimension of oblong threads in engagement with female threads of the side screw port according to an embodiment of the disclosure.
Figure 37B:
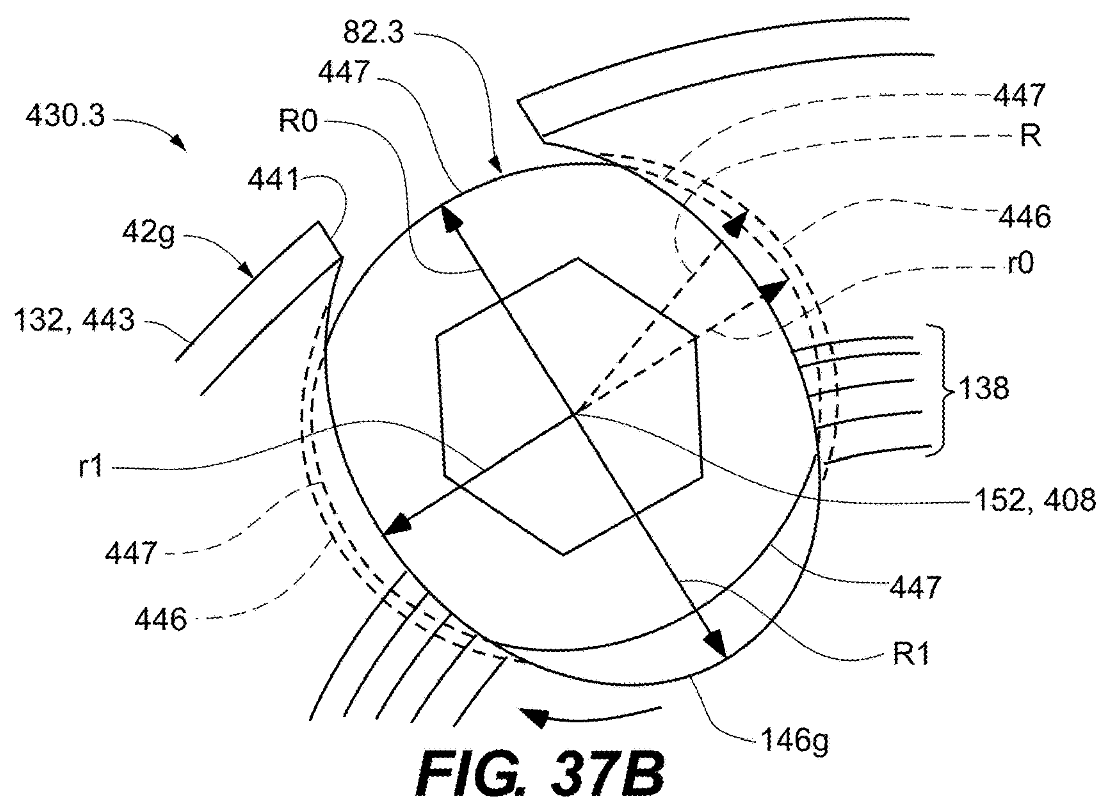
FIG. 37B is an enlarged, partial perspective view of FIG. 35B with the side screw of FIG. 36 disposed within a side screw port in an equipoise position, having a minor dimension of oblong threads in engagement with female threads of the side screw port according to an embodiment of the disclosure.

In operation, the side screw 82.3 is screwed into a bone and the oblong threads 447 of the side screw 82.3 brought into engagement with the side screw port 146*g* of the primary screw 42*g*. Because of the though hole of the side screw port 146*g* is oblong, there is more contact surface between the female threads 446 and the oblong threads 447 as the major radius R0 of the oblong threads 447 is rotated within the circular female threads 446 into alignment with the major radius R1 of the side screw port 146*g* (FIG. 37A, depicting the major radius R0 of the oblong threads 447 in phantom lodged within the female threads 446), the resistance to turning the side screw 82.3 within the female threads 446 decreases. As the major radius R0 of the oblong threads 447 are rotated out of alignment with the major radius R1 of the side screw port 146*g* and into alignment with the minor radius r1 of the side screw port 146*g*, the resistance to turning the side screw 82.3 within the female threads 446 decreases because there is diminishing overlap between the oblong threads 447 and the circular female threads 446. There is minimum overlap between the oblong threads 447 and the circular female threads 446 when the major radius R0 of the oblong threads is aligned with the major radius R1 of the side screw port 146*g* (FIG. 37B).

Functionally, the oblong threads 447 maintain threaded engagement with the female threads 446 of the side screw port 146*g* as the side screw 82.3 is driven into the bone, thereby establishing a stable axial relationship between the side screw 82.3 and the primary screw 42*g*. For embodiments where the pitch of the threads 446 and 447 are the same pitch as the threads of the side screw 82*c*, the axial tension that the side screw 82.3 exerts on the bone is reduced relative to embodiments where the pitch of the threads 446 and 447 are different from the pitch of the threads of the side screw 82*c*, so that the side screw 82.3 can be backed out and then retightened without exerting additional fatigue on the bone due to mismatched thread pitches.

Upon being driven into place, the side screw 82.3 is oriented so that the major radius R0 is aligned with the major radius R1 of the side screw port 146*g*, with the minor radius r0 of the oblong threads 447 being aligned with the minor radius r1 of the side screw port 146*g* and extending into and engaging the circular female threads 446. In this orientation, the minor radius r0 of the oblong threads 447 are engaged and centered within the threads 446 of the side screw port 146*g* at a position of minimum overlap (FIG. 37B). Because the overlap is minimum, the side screw 82.3 is in a state of equipoise when in the position illustrated in FIG. 37B. That is, in the position illustrated in FIG. 37B, the rotational forces on the side screw 82.3 are substantially balanced so that there is no motivation for the side screw 82.3 to rotate. Accordingly, while a surgeon may readily rotate the side screw 82.3 out of equipoise during implantation, the forces encountered by the side screw 82.3 after final implantation (e.g., vibration, flexing) are not enough to rotate the side screw 82.3 out of equipoise. As such, the side screw 82.3 will tend to remain in the equipoise position after implantation, so that the side screw 82.3 is effectively secured rotationally in the implanted equipoise orientation of FIG. 37B. In some embodiments, the torsional resistance to rotating the side screw 82.3 out of equipoise is in a range of 1.5 inch-pounds to 4 inch-pounds inclusive. In some embodiments, the torsional resistance to rotating out of equipoise is in a range of 2 inch-pounds to 3 inch-pounds inclusive.

Figure 38:
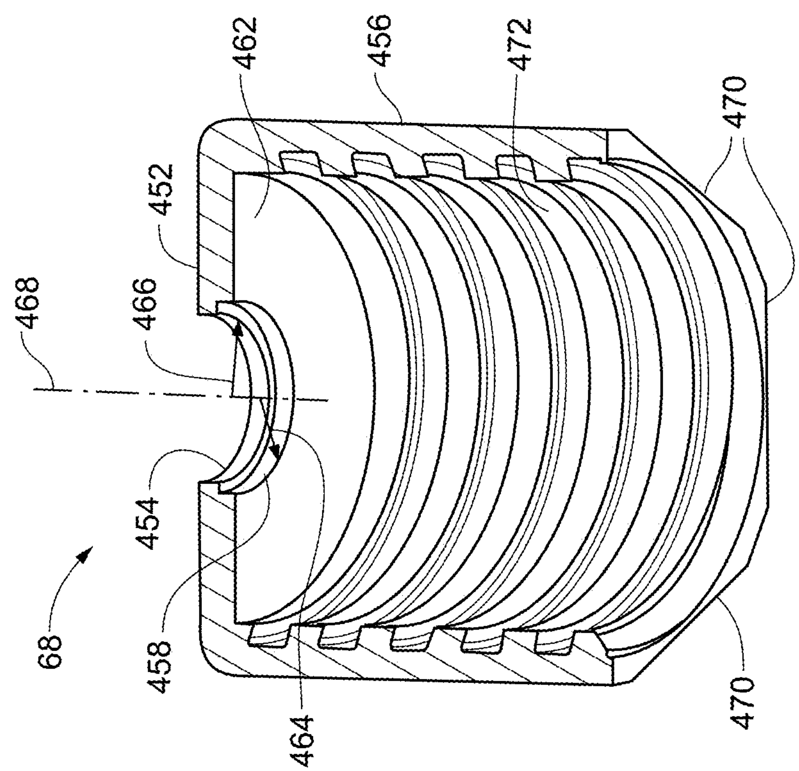
FIG. 38 is an enlarged, sectional view of a drive cap of FIG. 1 according to an embodiment of the disclosure.

Referring to FIG. 38, an enlarged sectional view of the drive cap 68 is described in further detail according to an embodiment of the disclosure. The drive cap 68 includes an end portion 452 defining a through-aperture 454 and from which a skirt portion 456 depends. An annular recess 458 is defined on an interior surface 462 of the end portion 452, the annular recess 458 defining an outer radius 464 and being open to an inner radius 466 of the through-aperture 454. The end portion 452, through-aperture 454, skirt portion 456, and annular recess 458 are concentric about a drive axis 468 of the drive cap 68. The exterior of the skirt portion 456 may define a plurality of flats 470, the flats 470 defining a polygonal cross-section such as a triangle, square, hexagon (depicted), or octagon.

The skirt portion 456 may define internal threads 472 configured to threadably engage the external threads 230 of the inserter 46. The inner radius 466 is dimensioned to enable the primary screw driver 48 to pass therethrough, including any ring guide 342 that may extend beyond the nominal radius 332 of the main body 334 of the shaft portion 320 of the primary screw driver 48. Accordingly, in such embodiments, the inner radius 466 is at least the maximum inner radius 394 of the keyway 392 defined in the ring 66. The annular recess 458 is configured to receive the ring 66 with a fit that enables the ring 66 to rotate within the annular recess 458. That is, the outer radius 464 of the annular recess 458 is dimensioned to enable the ring 66 to slidably rotate within the annular recess 458 when the ring 66 is seated within the annular recess 458.

Figure 39:
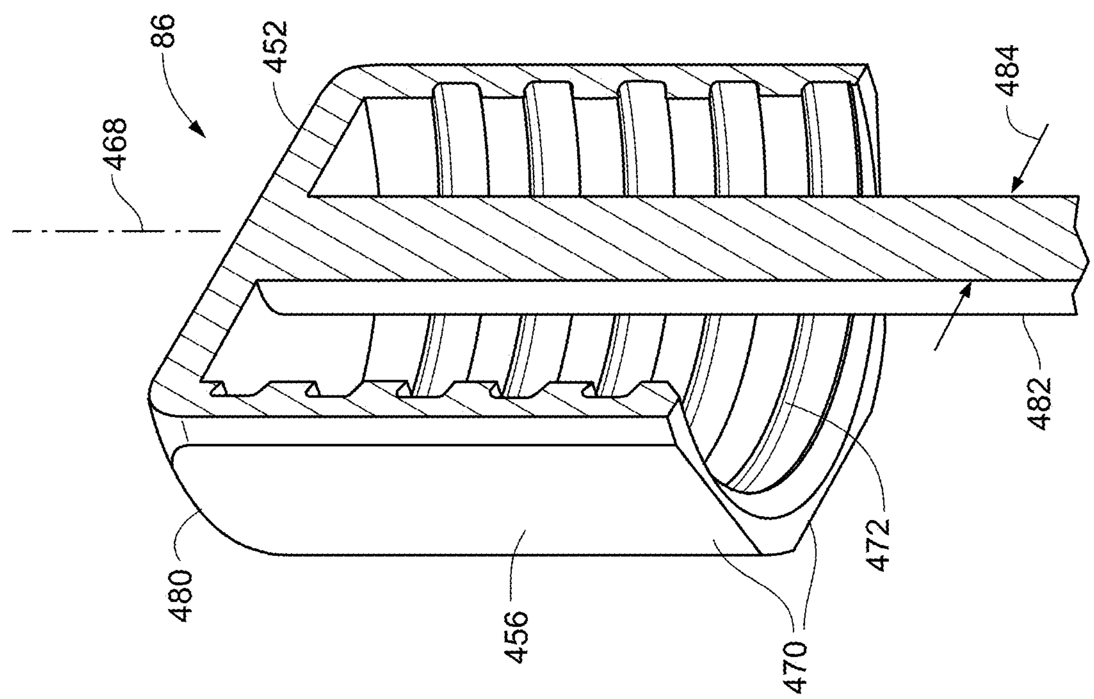
FIG. 39 is a partial, enlarged sectional view of a proximal end of a plunger of FIG. 1 according to an embodiment of the disclosure.

Referring to FIG. 39, a sectional view of the plunger assembly 86 is described in further detail according to an embodiment of the disclosure. The plunger assembly 86 includes a cap 480 that may have many of the same components and attributes as the drive cap 68, some of which are indicated by same-labeled reference characters. A plunger stem 482 defines an outer diameter 484 and depends from the end portion 452, extending axially beyond the skirt portion 456.

Referring to FIGS. 40 and 41, perspective views of the multifunctional handle 88 is described in further detail according to an embodiment of the disclosure. In some embodiments, the multifunctional handle 88 includes a body portion 502 that separates opposed first and second handle portions 504 and 506, the body portion 502 and opposed handle portions 504 and 506 being arranged along a lateral axis 508. The body portion 502 defines a socket 512 accessible from a first side 514 of the body portion 502 and a through-aperture 516 that extends from the socket 512 through the body portion 502. The socket 512 and through-aperture 516 are concentric about a central handle axis 518, the central handle axis 518 being perpendicular to the lateral axis 508. The first handle portion 504 may also define a socket 522 and through-aperture 526 that extends from the socket 522 through the first handle portion 504, the socket 522 and through aperture 526 being concentric about a first handle axis 528 that is perpendicular to the lateral axis 508. In some embodiments, the second handle portion 506 also defines a socket 532 that is concentric about a second handle axis 538, the second handle axis 538 being perpendicular to the lateral axis 508.

The socket 512 of the body portion 502 is configured for detachable coupling with the flats 470 of the drive cap 68 and the cap 480 of the plunger assembly 86. Accordingly, in the depicted embodiment, the socket 512 defines the hexagonal shape of the drive cap 68 and the cap 480 of the plunger assembly 86. The socket 522 of the first handle portion 504 is configured for detachable coupling with the wrench flats 330 of the primary screw driver 48. Accordingly, for the depiction of multifunctional handle 88, the socket 522 defines the hexagonal shape of the wrench flats 330 of the primary screw driver 48. The socket 532 of the second handle portion 506 is configured for detachable coupling with the proximal end of the guide rod 52 or optional side screw driver 84. Accordingly, in the depicted embodiment, the socket 532 defines the hexagonal shape of the proximal end 423 of the side screw driver 84. It is recognized that each of the sockets 512, 522, and 532 may be formed to shapes other than hexagonal, to accommodate whatever shape the caps 68 and 480, wrench flats 330, and proximal end 304 may define.

Figure 42:
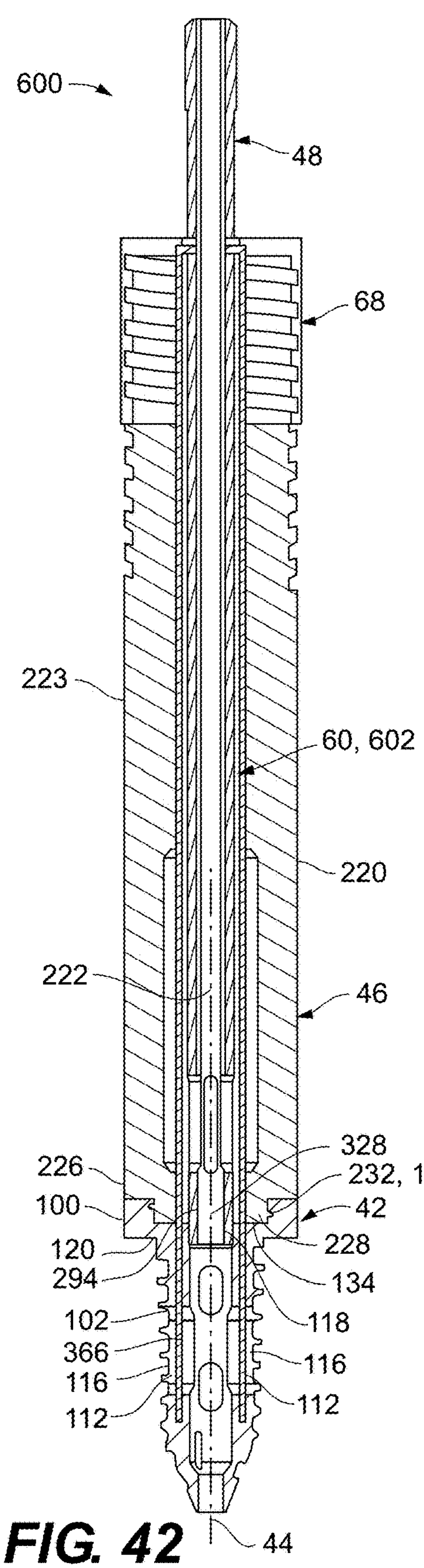
FIG. 42 is an elevational, sectional view of an initial assembly of the primary screw, inserter, primary screw driver, blade assembly, and drive cap of FIG. 1 according to an embodiment of the disclosure.
Figure 43:
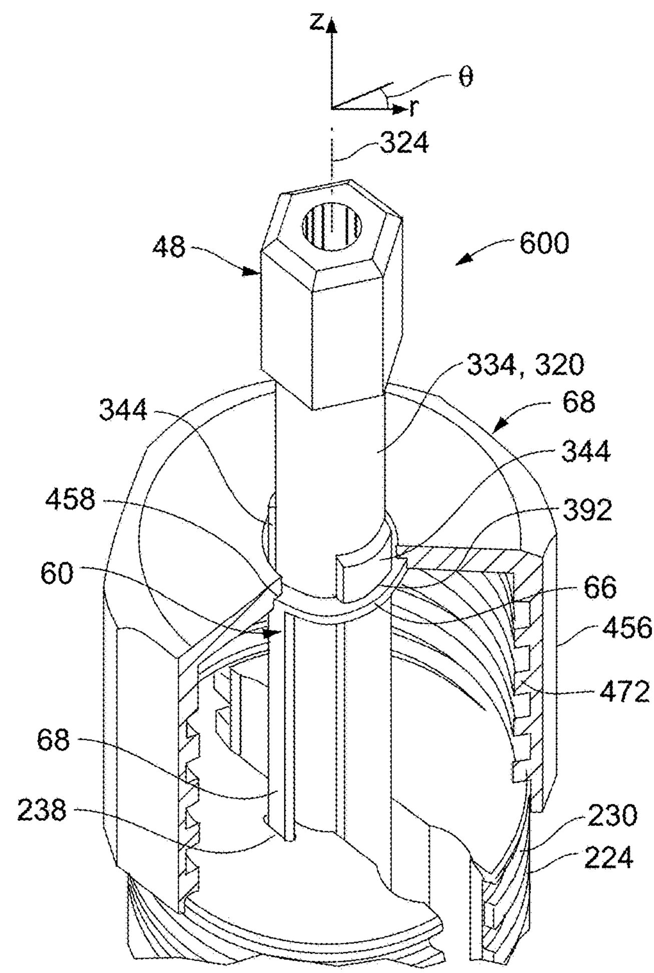
FIG. 43 is a partial sectional view of the initial assembly of the primary screw, inserter, and primary screw driver of FIG. 1 orthogonal to the sectional view of FIG. 42 according to an embodiment of the disclosure.
Figure 44:
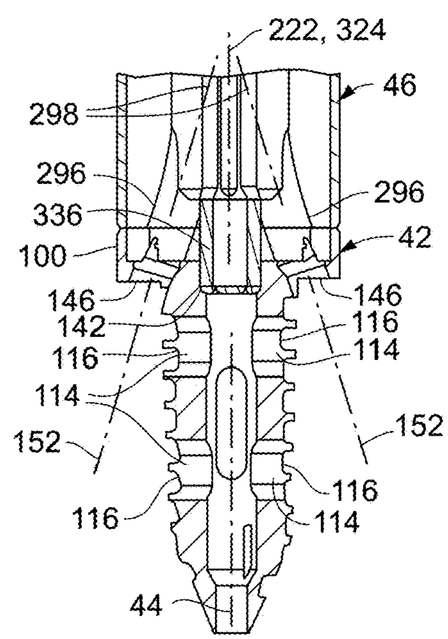
FIG. 44 is an enlarged, perspective cutaway view of a proximal end of the initial assembly of FIG. 42 according to an embodiment of the disclosure.

Referring to FIGS. 42 through 44, an initial assembly 600 of the primary screw 42, inserter 46, primary screw driver 48, blade assembly 60, and drive cap 68 is depicted according to an embodiment of the disclosure. For the initial assembly 600, the boss 228 of the inserter 46 is inserted into and rotated within the recess 134 of the primary screw 42 so the exterior thread 232 of the boss 228 is fully engaged with the interior thread 138 of the inner circular wall portions 136 of the flange 132 surrounding the recess 134. The inserter axis 222 and central egress port 294 of the main cylinder 220 is thereby aligned with the central axis 44 and opening 118 at the proximal end 120 of the body portion 102 of the primary screw 42. The threads 138, 232 may be fully engaged after, for example, a ¼ turn, ½ turn, or full turn between the inserter 46 and the primary screw 42. When the threads 138, 232 are fully engaged, the head 100 of the primary screw 42 registers against the distal end 226 of the main cylinder 220, effectively capping the distal end 226 and boss 228 of the inserter 46. In some embodiments, the primary screw 42 and inserter 46 are configured so that, when the threads 138, 232 are fully engaged, the canted axes 298 of the side egress ports 296 side screw ports are aligned with the side screw port axes 152 of the screw side ports 146 of the primary screw 42.

Also during the buildup of the initial assembly 600, the blade assembly 60 is disposed in the inserter 46. The elongate blades 62 are inserted into the blade passages 238 of the inserter 46 at the proximal face 242 of the main cylinder 220, through the blade passages 238 and into the blade passages 162 of the primary screw 42. For the initial assembly 600, the distal portions 366 of the elongate blades 62 extend axially through the elongate side ports 112. Also in the initial assembly 600, the blade assembly 60 defines a retracted configuration 602, wherein the distal portions 366 of the elongate blades 62 extend parallel to and are adjacent the external opening 116 of the elongate side port 112.

For the initial assembly 600, the drive cap 68 is mounted to the inserter 46. The drive cap 68 is aligned over the blade assembly 60 and the internal threads 472 of the skirt portion 456 brought into engagement with the external threads 230 at the proximal end 224 of the inserter 46. The inserter 46 and drive cap 68 are configured so that the annular recess 458 of the drive cap 68 seats on the ring 66 of the blade assembly 60 when the internal threads 472 of the skirt portion 456 are initially started on the external threads 230 of the main cylinder 220 of the inserter 46.

The primary screw driver 48 is inserted through the mounted drive cap 68. The distal end 328 of the primary screw driver 48 is inserted first, and the primary screw driver 48 rotationally oriented so that the rails 344 are aligned with the keyways 392 of the ring 66 of the blade assembly 60. The primary screw driver 48 is then further inserted until the driving head 336 reaches the primary screw 42. In some embodiments, the rails 344 are positioned on the main body 334 of the shaft portion 320 so that, when the rails 344 are aligned with the keyways 392 and the central axis 324 of the main body 334 is aligned with the central axis 44 of the primary screw 42, the driving head 336 is rotationally aligned with the shape of the socket 142 of the primary screw 42 for insertion into the socket 142. In some embodiments, upon insertion of the driving head 336 into the socket 142, the rails 344 are resident in the keyways 392 of the ring 66.

The above description refers to the blades 62, elongate side ports 112, side screw ports 146, side screw port axes 152, blade passages 162, 238, side egress ports 296, canted axes 298, rails 344, and keyways 392 in the plural. It is understood that the embodiments having a single blade 62, elongate side port 112, side screw port 146, side screw port axis 152, blade passage 162, 238, side egress port 296, canted axis 298, rail 344, or keyway 392 is also contemplated, and that accommodating such modifications, guided by the present disclosure, are readily understood by the artisan of ordinary skill.

Figure 45:
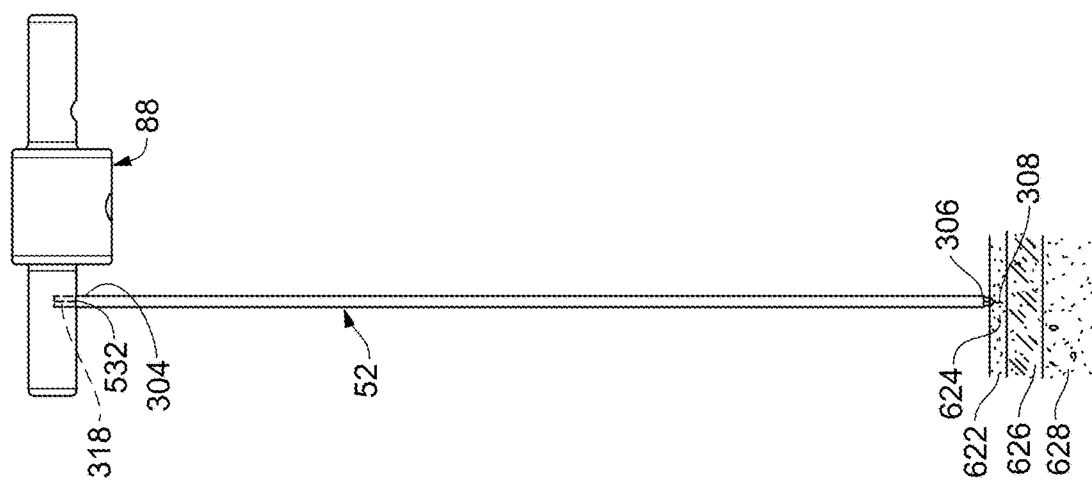
FIG. 45 is an elevational view of the guide rod of FIG. 22 in operation according to an embodiment of the disclosure.

Referring to FIGS. 45 through 54, implantation of the primary screw 42 is depicted according to an embodiment of the disclosure. The distal end 306 of the guide rod 52 is placed in contact a first bone 622 (e.g., the ilium) at a desired penetration site 624. The socket 532 of the multifunctional handle 88 is coupled to the flats 318 of the proximal end 304 of the guide rod 52 and the guide rod 52 rotated with the multifunctional handle 88 to tap the self-tapping threaded structure 308 into the first bone 622 (FIG. 45).

Figure 46:
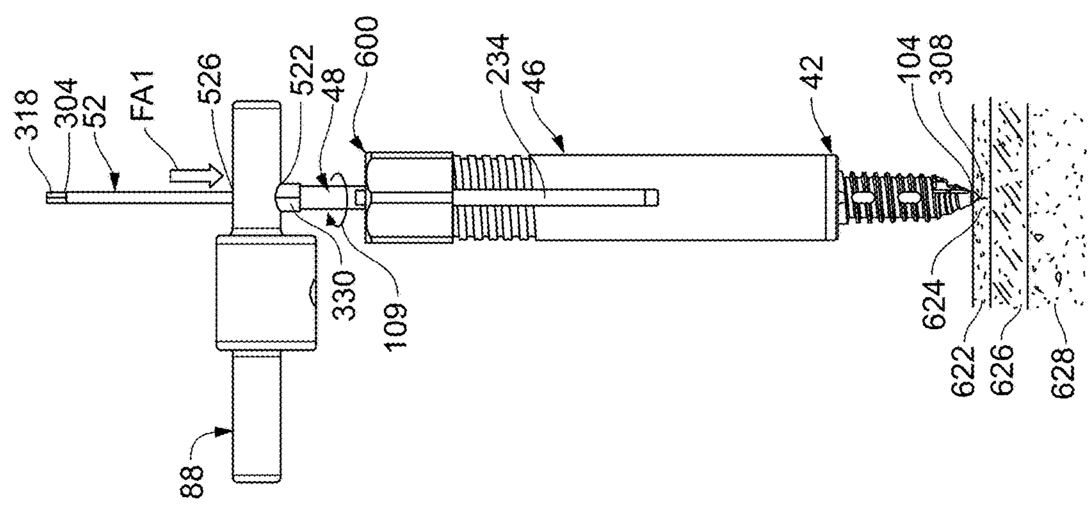
FIG. 46 is an elevational view of the initial assembly of FIG. 42 in operation over the guide rod of FIG. 45 according to an embodiment of the disclosure.

After the guide rod 52 is anchored to the first bone 622, the multifunctional handle 88 is decoupled from flats 318 of the guide rod 52 and the initial assembly 600 slid over the guide rod 52 so that the tip portion 104 of the primary screw 42 is brought into contact with the first bone 622 at the desired penetration site 624. The socket 522 and through-aperture 526 of the multifunctional handle 88 is slid over the guide rod 52 and the socket 522 mated with the wrench flats 330 of the primary screw driver 48. An axial force FA1 is applied to the primary screw driver 48 as the primary screw driver 48 is rotated in the cutting rotational direction 109 with the multifunctional handle 88 to drive the primary screw 42 into threaded engagement with the first bone 622 (FIG. 46).

Figure 47:
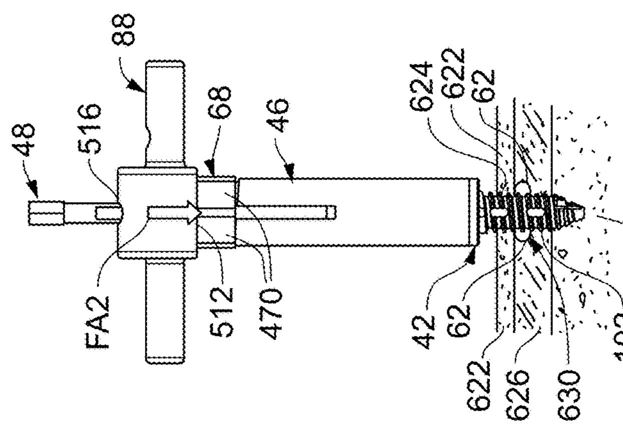
FIG. 47 is an elevational view of the initial assembly of FIG. 42 with the blades deployed during implantation of the primary screw according to an embodiment of the disclosure.

The primary screw 42 is thereby driven through the first bone 622, a tissue layer 626 (e.g., cartilage), and into a second bone 628 (e.g., the sacrum). At this point in the implantation process, the guide rod 52 may be detached from the first bone 622 and withdrawn from the inserter 46. As the elongate side ports 112 enter the tissue layer 626, the blades 62 of the blade assembly 60 may be deployed. To deploy the blades 62, the socket 512 and through-aperture 516 of the body portion 502 of the multifunctional handle 88 are slid over the primary screw driver 48 so that the socket 512 mates with the flats 470 of the drive cap 68. In some embodiments, the inserter 46 is grasped and held stationary while the drive cap 68 is drawn tight over the external threads 230 of the main cylinder 220 of the inserter 46. As the drive cap 68 is drawn onto the inserter 46, the annular recess 458 of the drive cap 68 rotates on the ring 66 of the blade assembly 60 (FIG. 43). The ring 66 is prevented from rotating by the guide 342 (e.g., rails 344) of the primary screw driver 48. Accordingly, rotation of the drive cap 68 onto the inserter 46 imparts an axial force FA2 on the blades 62 without twisting the blades 62. The axial force FA2 causes the blades 62 to deflect radially outward into a deployed configuration 630 and into the tissue layer 626 (FIG. 47). In the deployed configuration 630, the blades 62 bow radially outward through the openings 116 of the elongate side ports 112 and radially beyond the body portion 102 of the primary screw 42.

With the blades 62 in the deployed configuration 630, or while the blades 62 are being deployed, rotation of the primary screw 42 is resumed. Resumption of the rotation of the primary screw 42 may be performed by driving the inserter 46 with the multifunctional handle 88 as arranged in FIG. 47, which in turn drives the primary screw 42. Optionally, the multifunctional handle 88 may be arranged as depicted in FIG. 46 to drive the primary screw 42 with the primary screw driver 48. The rotational action of the deployed blades 62 as the primary screw 42 is driven further into the penetration site 624 cuts a zone 632 out of the tissue layer 626, which can be seen in FIG. 49. The zone 632 may be annular, surrounding the primary screw 42. In some embodiments, blades 62 remain in the deployed configuration 630 until the primary screw 42 reaches full implantation depth (i.e., until the head 100 of the primary screw 42 is firmly seated on the first bone 622). In other embodiments, the blades 62 are retracted before the primary screw 42 reaches full implantation depth, to prevent the blades from grinding into the second bone 628.

Figure 48:
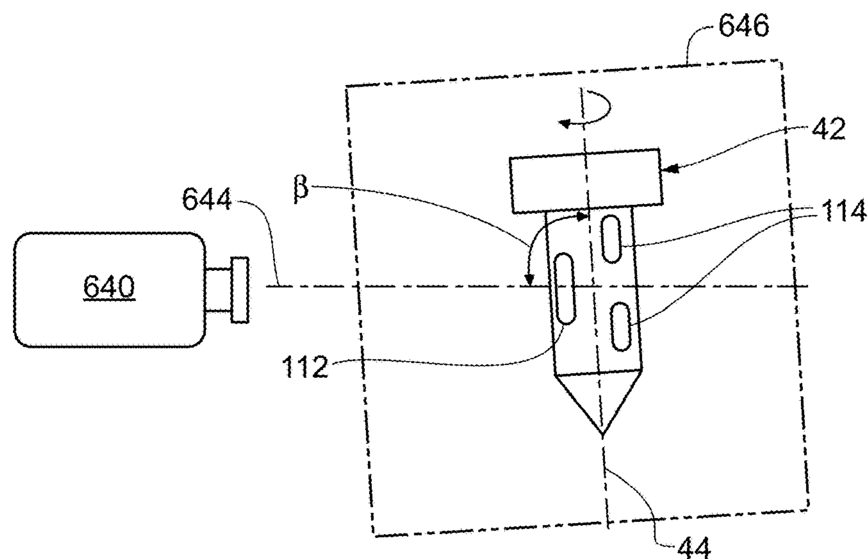
FIG. 48 is a schematic view of a surgical imaging device for rotationally aligning an implanted primary screw according to an embodiment of the disclosure.
Figure 48A:
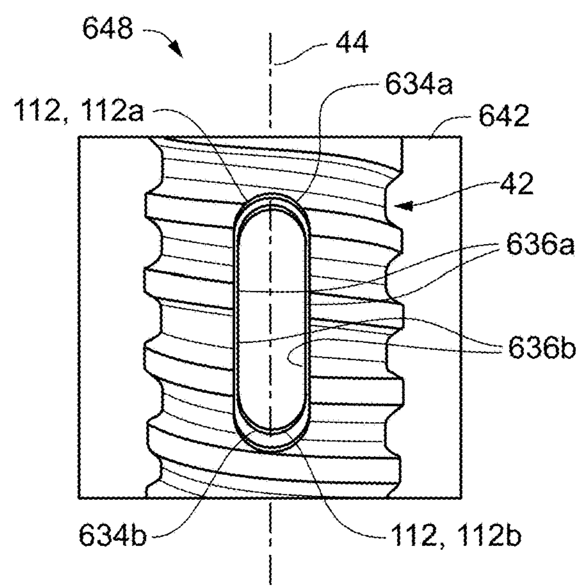
FIG. 48A is a three-dimensional image of aligned elongate side ports for determining the orientation of the primary screw according to an embodiment of the disclosure.
Figure 48B:
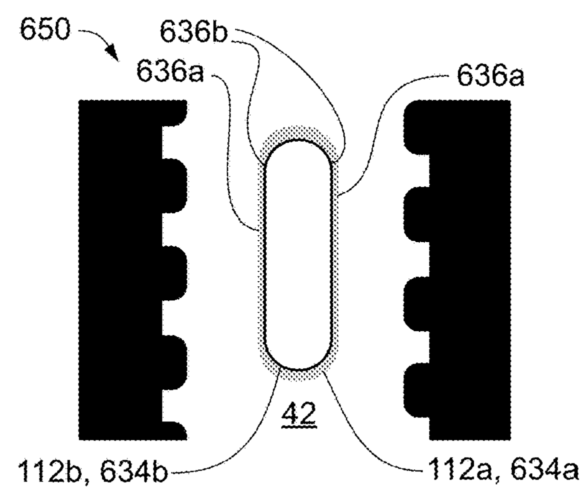
FIG. 48B is an image of FIG. 48A generated by the surgical imaging device of FIG. 48 according to an embodiment of the disclosure.

In some embodiments of the disclosure, and in reference to FIGS. 48 through 48B, a surgical imaging device 640 is utilized for rotationally aligning the primary screw 42 in a desired orientation for placement of the side screws 82 once the primary screw 42 is implanted at approximately full implantation depth. The surgical imaging device 640 defines a field of view 642 centered about a viewing axis 644.

The surgical imaging device 640 is arranged to laterally view the central axis 44 and so that the viewing axis 644 is coplanar with a desired alignment plane 646. Herein, to "laterally view" the central axis 44 is to have the central axis 44 extend across a field of view 642 of the surgical imaging device 640. In one embodiment, the desired alignment plane 646 is orthogonal to the plane of the side screw port axes 152 when the primary screw 42 is properly aligned. Alternatively, the desired alignment plane 646 may be coplanar with the plane of the side screw port axes 152 upon proper alignment. The surgical imaging device 640 is sighted along the desired alignment plane 646 so that the viewing axis 644 intersects the central axis 44 at an angle β. While the angle β preferably approximates a 90 degree angle, other angles may also be utilized. The viewing axis 644 need only be coplanar with the desired alignment plane 646 for proper alignment of the side screw port axes 152.

In some embodiments, the elongate side ports 112 are utilized for the rotational alignment of the primary screw 42. Herein, the elongate side ports 112 are identified individually as first and second elongate side ports 112*a* and 112*b*, located on the first and second lateral sides 111*a* and 111*b*, respectively, of the primary screw 42. The elongate side ports 112*a* and 112*b* may be identical in shape and size, with each defining respective perimeters 634*a* and 634*b* having axially extending tangential edges 636*a* and 636*b*. In some embodiments, the tangential edges 636 are linear and extend parallel to each other (depicted).

In FIGS. 48A and 48B, the second elongate side port 112*b*, which is furthest from the surgical imaging device 640, appears to be within the first elongate side port 112*a*, which is nearer the surgical imaging device 640, even though the side ports 112*a* and 112*b* may be of identical dimension. The appearance of the side port 112*b* being within the side port 112*a* in two dimensions arises because of the focal depth of the surgical imaging device 640, Certain candidate materials for the primary screw 42, such as titanium, are known to be semi-transparent to x-rays. More of the x-rays that pass through thicker or multiple thicknesses of material will be absorbed or otherwise attenuated by the material, while x-rays that pass through no material experience only light or incidental attenuation.

To rotationally align the primary screw 42 in the desired orientation using the elongate side ports 112, the primary screw 42 is rotated so that the first lateral side port 112*a* nearest the surgical imaging device subtends the viewing axis 644. The primary screw 42 is then rotationally adjusted until both of the tangential edges 636*b* of the second lateral side port 112*b* are visible through the first lateral side port 112*a*. An example of an aligned orientation 648 of the lateral side ports 112 is presented in FIG. 48A for a primary screw 42 that is rotationally aligned along the viewing axis 644. A representation of a corresponding image 650 produced by the surgical imaging device 640 is depicted in FIG. 48B for an x-ray imaging device.

Figure 48C:
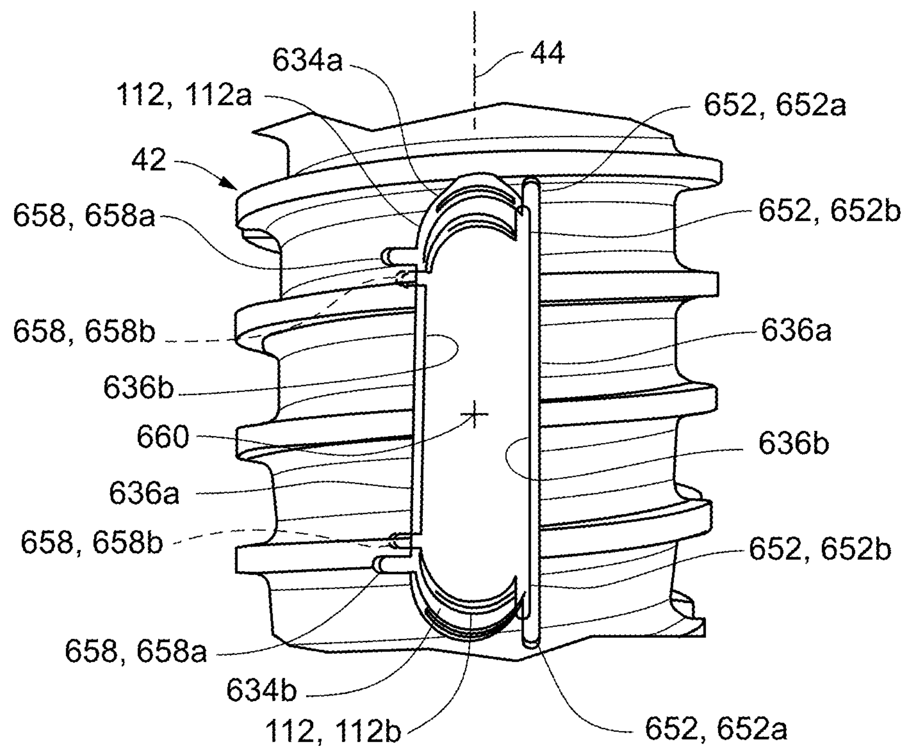
FIG. 48C is a three-dimensional image of aligned elongate side ports having vertical alignment notches that are tangential to the elongate side ports and lateral alignment notches, for determining the orientation of the primary screw according to an embodiment of the disclosure.

In some embodiments, and in reference to FIGS. 48C through 48I, each of the perimeters 634*a* and 634*b* define a pair of axial notches 652*a* and 652*b*, respectively (referred to collectively or generically as axial notches 652). The axial notches 652 extend substantially parallel to the central axis 44 of the primary screw 42. The axial notches 652*a* and 652*b* are depicted in FIG. 48C as extending axially from the tangential edges 636*a* and 636*b*, respectively, with a representation of a respective corresponding image 654 depicted in FIG. 48D.

Figure 48D:
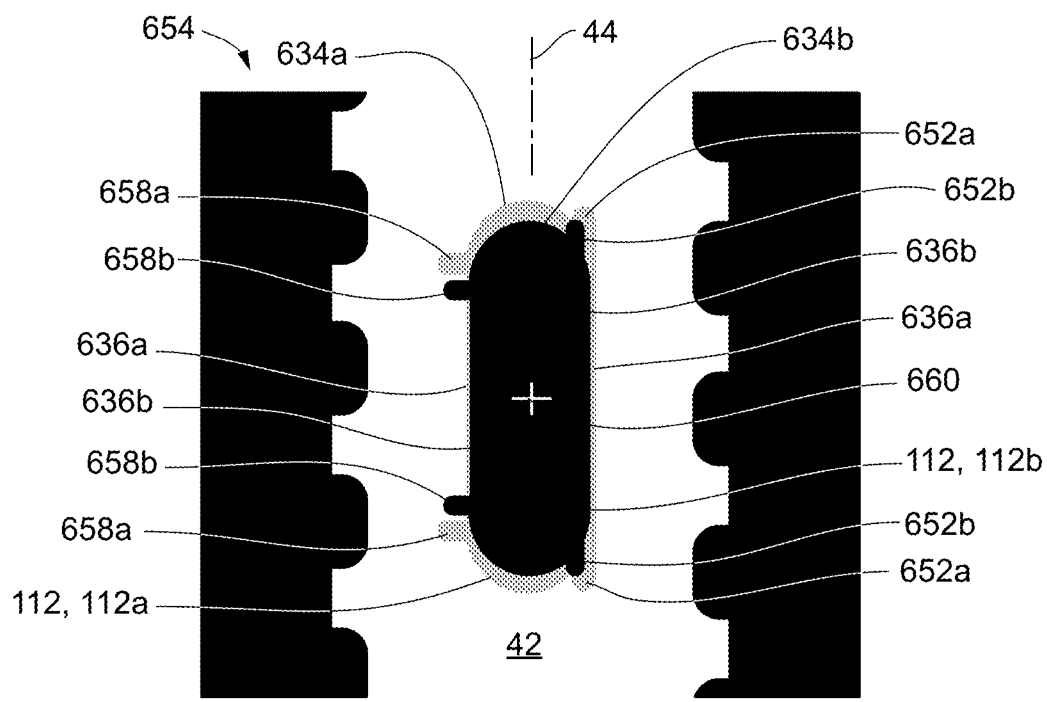
FIG. 48D is an image of FIG. 48C generated by the surgical imaging device of FIG. 48 according to an embodiment of the disclosure.
Figure 48E:
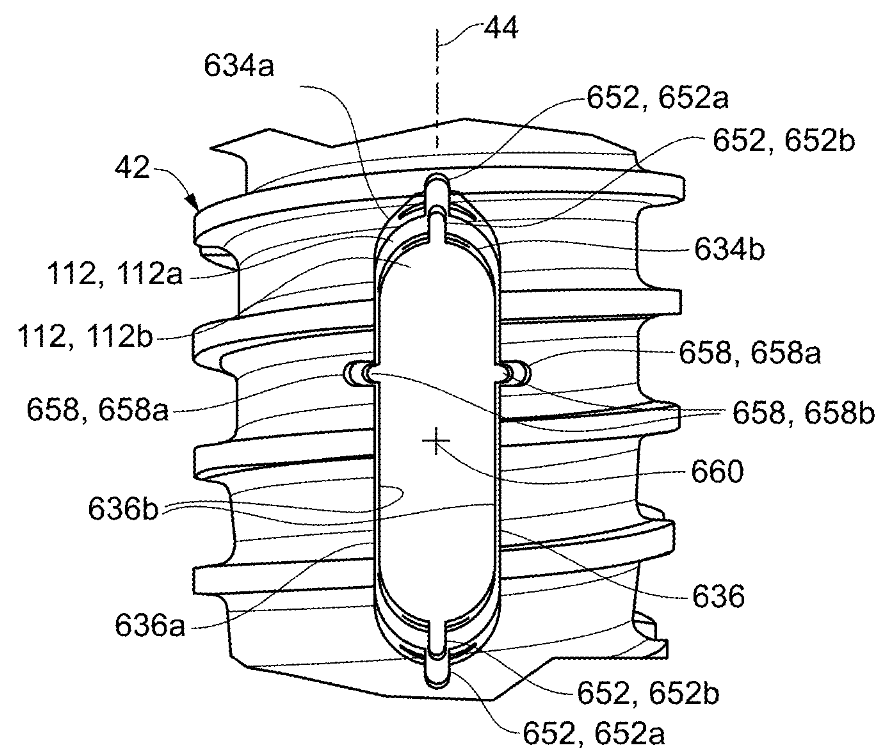
FIG. 48E is a three-dimensional image of aligned elongate side ports having vertical alignment notches that centered with respect to the elongate side ports and lateral alignment notches, for determining the orientation of the primary screw according to an embodiment of the disclosure.
Figure 48F:
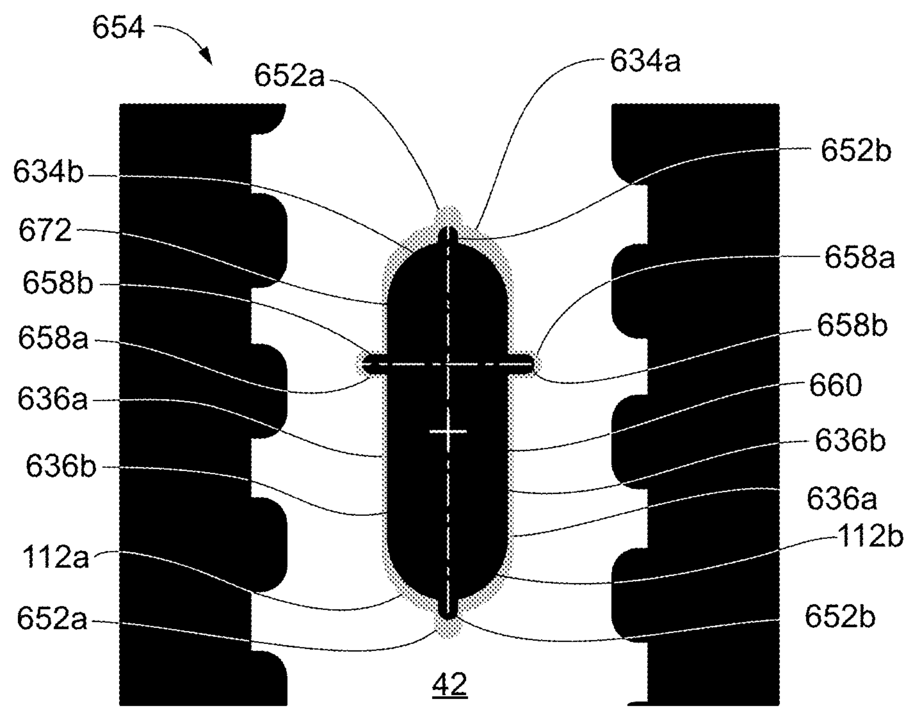
FIG. 48F is an image of FIG. 48E generated by the surgical imaging device of FIG. 48 according to an embodiment of the disclosure.

In FIG. 48E, both lateral side ports 112*a* and 112*b* and both pairs of axial notches 652*a* and 652*b* are depicted as being centered in diametric opposition along a central lateral axis 660 that passes through the central axis 44 and is coplanar with the mid-plane 174. As such, the axial notch pairs 652*a* and 652*b* are tangentially centered with respect to the perimeters 634*a* and 634*b*, respectively. A representation of a respective image 656 corresponding to the view of FIG. 48E is depicted in FIG. 48F.

Figure 48I:
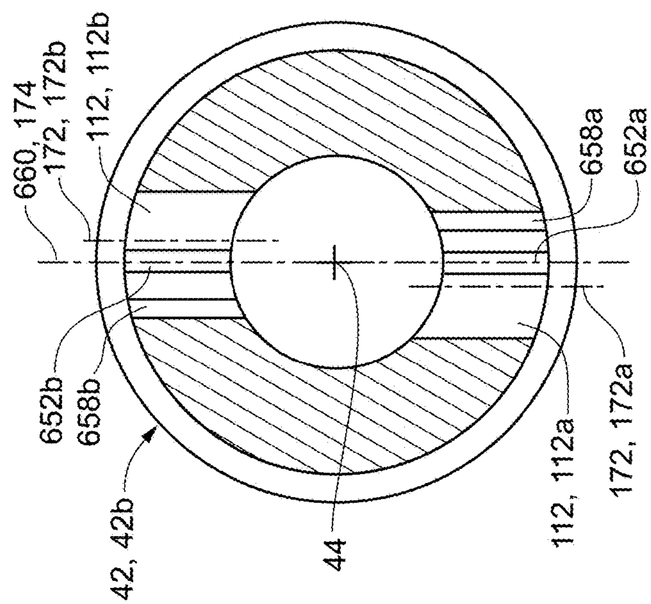
FIG. 48I is a sectional view along plane I-I of FIG. 48G.
Figure 48G:
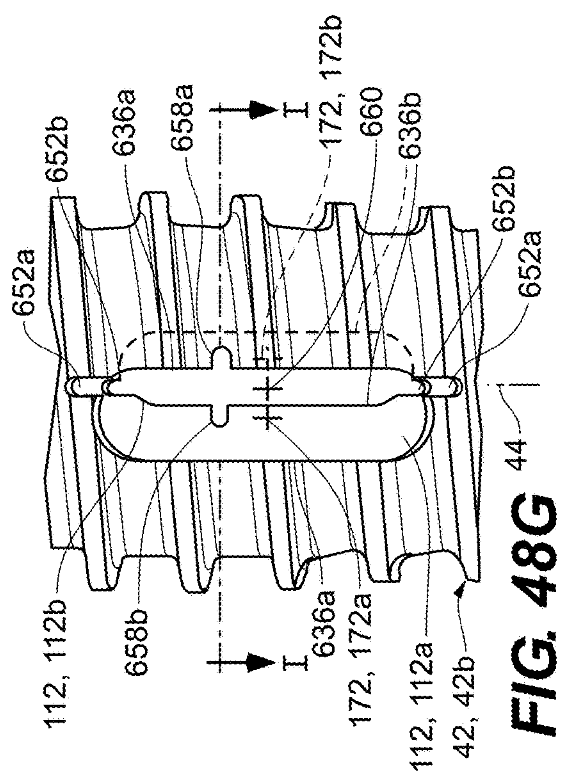
FIG. 48G is a three-dimensional image of aligned axial and lateral alignment notches for elongate side ports that are offset, for determining the orientation of the primary screw according to an embodiment of the disclosure.

In FIG. 48G, which portrays alignment of primary screw 42*b* of FIGS. 8 through 8B, the lateral side ports 112*a* and 112*b* are centered about their respective offset lateral axes 172*a* and 172*b* that are laterally offset from the central axis 44. However, the axial notch pairs 652*a* and 652*b* are centered in diametric opposition along the central lateral axis 660 that passes through the central axis 44. The relationship between the offset lateral axes 172*a* and 172*b* and the central lateral axis 660 is depicted in FIG. 48I. As such, the axial notch pairs 652*a* and 652*b* are not centered with respect to the respective lateral side port 112*a* and 112*b*.

Figure 48H:
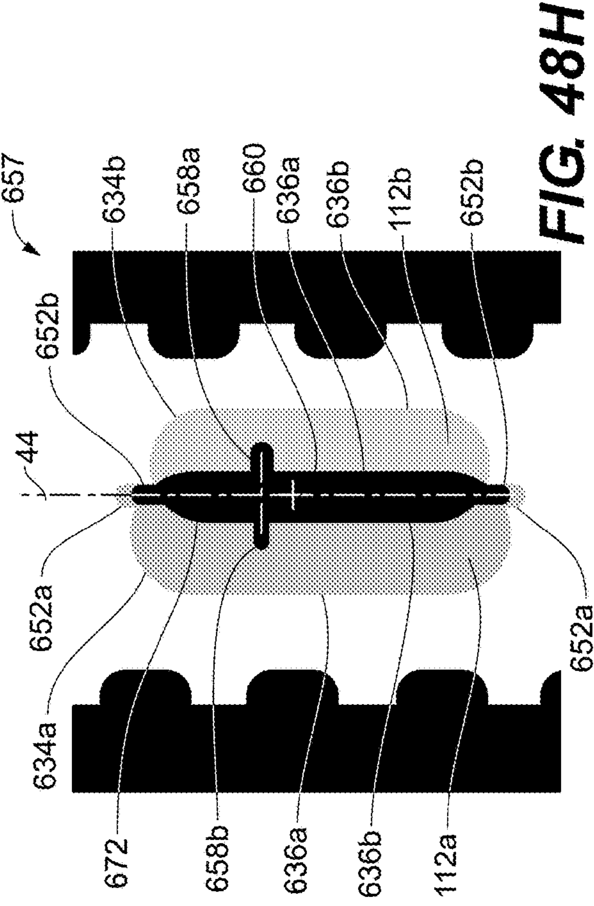
FIG. 48H is an image of FIG. 48G has generated by the surgical imaging device of FIG. 48 according to an embodiment of the disclosure.
Figure 51:
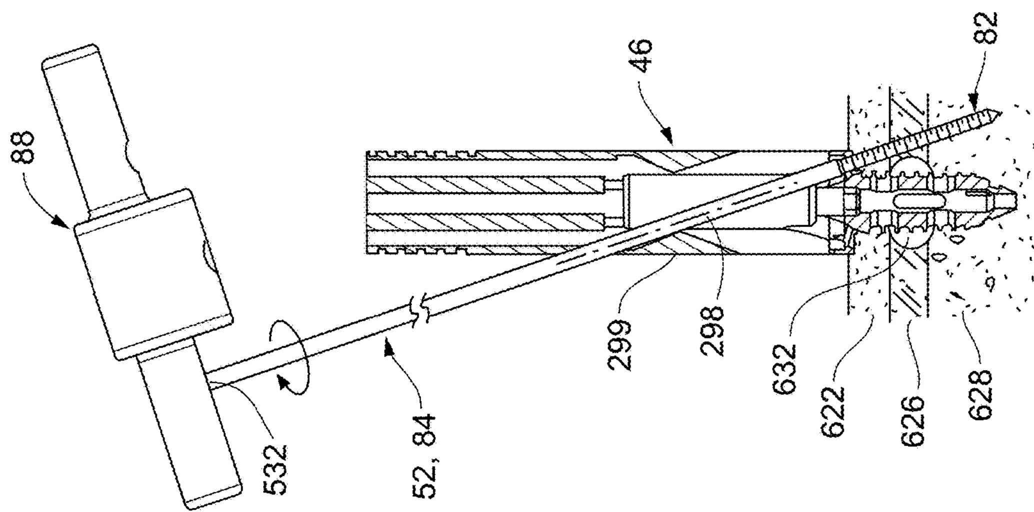
FIGS. 49-51 are sectional views of the inserter and primary screw configured for the routing of the side screw of FIG. 30 through the inserter and being implanted for the anchoring of the primary screw according to an embodiment of the disclosure.

A representation of a respective image 657 corresponding to the view of FIG. 48G is depicted in FIG. 48H.

In some embodiments, each of the perimeters 634*a* and 634*b* define at least one tangential notch 658*a* and 658*b*, respectively (referred to collectively or generically as tangential notch(es) 658). The tangential notch(es) 658 extend substantially orthogonal to the central axis 44 of the primary screw 42. In FIG. 48C, the tangential notches 658*a* and 658*b* are depicted as extending tangentially from one of the tangential edges 636*a* and 636*b*, respectively, with a representation of the respective corresponding image 654 depicted in FIG. 48D.

In FIG. 48E, the tangential notches 658*a* and 658*b* are depicted as being axially centered with respect to the perimeters 634*a* and 634*b*, respectively, and extending from both the tangential edges 636*a* and 636*b*, respectively, with the representation of the respective corresponding image 656 depicted in FIG. 48F. The axial notches 652 and the tangential notches 658 of FIGS. 48E and 48F in effect represent the axial and lateral ends of a reticle pattern 672, depicted with dashed lines in FIG. 48F.

In FIGS. 48G and 48I, a single tangential notch 658*a* is defined as extending from one of the tangential edges 636*a*. The tangential edge 636*a* from which the tangential notch 658*a* extends is the tangential edge 636*a* that is closer to the central lateral axis 660. Likewise, a single tangential notch 658*b* is defined as extending from one of the tangential edges 636*b*, with the tangential edge 636*b* from which the tangential notch 658*a* extends being the tangential edge 636*a* that is closer to the central lateral axis 660. The representation of the respective corresponding image 657 depicted in FIG. 48H. When aligned along the central lateral axis 660, the axial notches 652 and the tangential notches 658 of FIGS. 48G and 48H in effect represent the axial and lateral ends of the reticle pattern 672, depicted with dashed lines in FIG. 48H.

Functionally, the axial notches 652, when implemented, assist in the rotational alignment of the primary screw 42. The primary screw 42 is rotated so that the lateral side port 112*a* nearest the surgical imaging device subtends the viewing axis 644. The primary screw 42 is then tweaked rotationally so that the axial notches 652*a* and the axial notches 652*b* are in axial alignment. Examples of aligned orientations of the axial notches 652 is presented in FIGS. 48C, 48E, and 48G for a primary screw 42 that is rotationally aligned along the viewing axis 644. Representations of corresponding images 654, 656, and 657 produced by the surgical imaging device 640 are depicted in FIGS. 48D, 48F, and 48H, respectively for an x-ray imaging device.

Note that for the primary screw 42*b* of FIG. 48G, alignment of the perimeters 634*a* and 634*b* of the lateral side ports 112*a* and 112*b* along the viewing axis 644 does not rotationally align the side screw ports 146 of the primary screw 42*b*. This is because the offset lateral axes 172*a* and 172*b* of the lateral side ports 112*a* and 112*b* are laterally offset relative to the central axis 44 and the central lateral axis 660. Accordingly, if the lateral side ports 112*a* and 112*b* were aligned along the viewing axis 644, the viewing axis 644 would not be aligned with the desired alignment plane 646. The axial notches 652, however, provide a feature such that, when the primary screw 42*b* is rotated so that the axial notches 652 are coplanar with the viewing axis 644, the viewing axis 644 is also coplanar with the central lateral 660 and the desired alignment plane 646.

Once the primary screw 42 is rotationally aligned, the separation between corresponding tangential notches 658 (when implemented) provides an indication of the pitch of the primary screw 42 with respect to the viewing axis 644. The image 654 of FIG. 48D depicts the tangential notches 658*a* and 658*b* as having small axial separation 674, indicating that the angle β between the central axis 44 of the primary screw 42 and the viewing axis 644 is approximately 90 degrees. The further the angle β deviates from 90 degrees, the greater the separation between the tangential notches 658.

The image 656 of FIG. 48F depicts the tangential notches 658*a* and 658*b* as being in alignment (i.e., as having essentially no axial separation) for the reticle pattern 672, indicating that the angle β between the central axis 44 of the primary screw 42 and the viewing axis 644 is approximately 90 degrees. The further the angle β deviates from 90 degrees, the greater the separation between the tangential notches 658 of the reticle pattern 672.

The representative images 650, 654, and 656 of FIGS. 48B, 48D, and 48F illustrate the effect of the semi-transparency of the material of the primary screw 42 to x-rays. The regions where x-rays pass through more than one wall thickness of screw material (e.g., that pass twice through the side wall 106 of the primary screw 42) are represented in white. Regions where x-rays do not pass through any of the screw material are represented in black. Regions where x-rays pass through only one wall thickness of screw material are represented in gray. While FIG. 48A is not an exact depiction of a screw in an x-ray image, those of skill in the relevant arts will recognize what the depiction of FIG. 48A represents—that the material immediately adjacent perimeter 634*b* is discernable from the material immediately adjacent perimeter 634*a* and can be viewed through perimeter 634*a* with the surgical imaging device 640. This enables the perimeter 634*b* to be distinguished from the perimeter 634*a*, thereby providing enhanced alignment capability.

In some embodiments, the foregoing methods are outlined on the instructions 92. The instructions 92 may be physically included with the kit 90 such as on a printed document (depicted), compact disc, or flash drive. In other embodiments, the instructions 92 may be provided remotely, for example on a hard drive of a remote server that is internet accessible with an electronic device such as a computer, smart phone, or electronic tablet. The instructions 92 may include text, photos, videos, or a combination thereof to instruct and guide the user.

Figure 49:
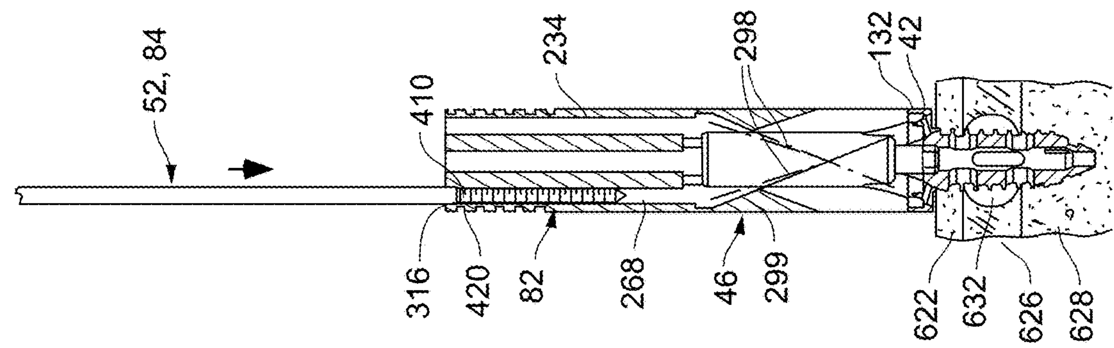

Once the primary screw 42 is at full implantation depth and rotationally oriented as desired, the drive cap 68, blade assembly 60, and primary screw driver 48 may be removed from the inserter 46 for installation of the side screws 82. The drive cap 68 is removed from the proximal end of the inserter 46, so that the elasticity of the blades 62 cause the blades 62 to return to a straight configuration. The primary screw driver 48 and blade assembly 60 are extracted proximally from the inserter 46, leaving only the inserter 46 and the primary screw 42. In some embodiments, the guide rod 52 is utilized to route and set the side screws 82. The driving head 316 of the guide rod 52 is press fit into the socket 420 of a first of the side screws 82. Alternatively, the side screw driver 84 is used instead, with the driving head 428 of the side screw driver 84 forming the press fit with the socket 420 the side screw 82. Using the guide rod 52 or side screw driver 84, the side screw 82 is inserted into the access slot 234 so that the head 410 of the side screw 82 is captured and guided by a first of the mirrored side arcuate channels 268 of the opposed inner surfaces 264 of the access slot 234 (FIG. 49). The side screw 82 is translated axially through the mirrored side arcuate channels 268 until encountering a first of the guide ramps 299. At the guide ramp 299, the distal end

Figure 50:
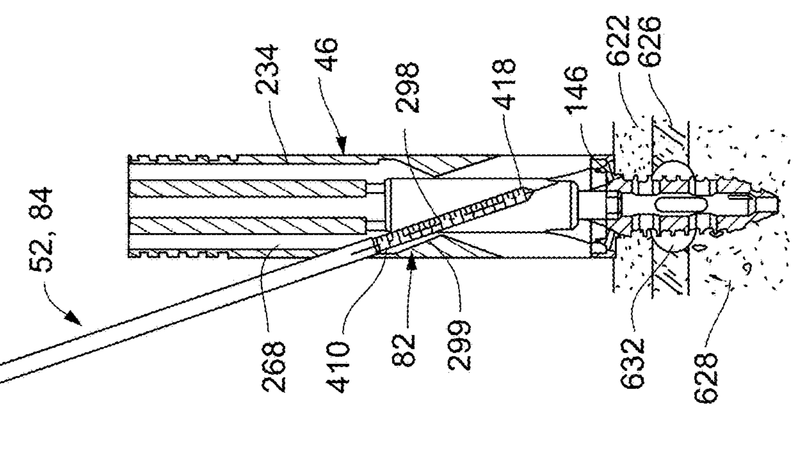

418 of the side screw 82 is rotated laterally inward with the guide rod 52 or side screw driver 84 as the head 410 is slid axially through the mirrored side arcuate channels 268 until the side screw 82 is substantially aligned with a first of the canted axes 298 (FIG. 50). The side screw 82 is then translated along the canted axis 298 to a first of the side screw ports 146. The socket 532 of the multifunctional handle 88 is fitted to the guide rod 52 or side screw driver 84 to drive and set the side screw 82 through the first bone 622, tissue 626, and second bone 628 (FIG. 44). Because the side screw 82 is firmly implanted in the bones 622 and 628, the light press fit between the driving head 316 of the guide rod 52 and the socket 420 of the side screws 82 is readily overcome by pulling the guide rod 52 out of the head 410 of the side screw 82. For the depicted embodiment, the procedure is repeated for the implantation of a second of the side screws 82, using a second of the mirrored side arcuate channels 268, a second of the guide ramps 299, a second of the canted axes 298, and a second of the side screw ports 146.

Figure 52:
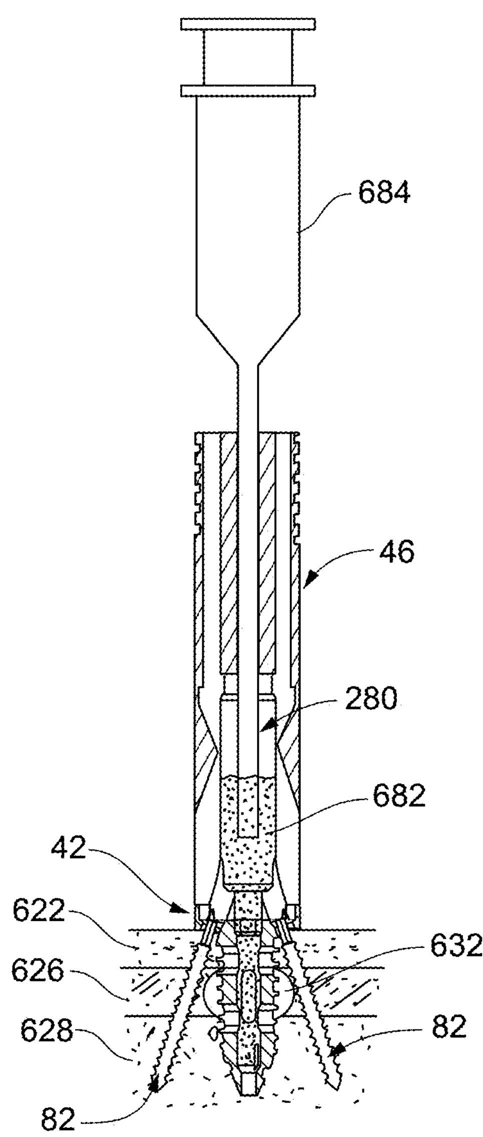
FIG. 52 is a sectional view of a grafting material being disposed in the inserter sleeve and implanted primary screw according to an embodiment of the disclosure.
Figure 53:
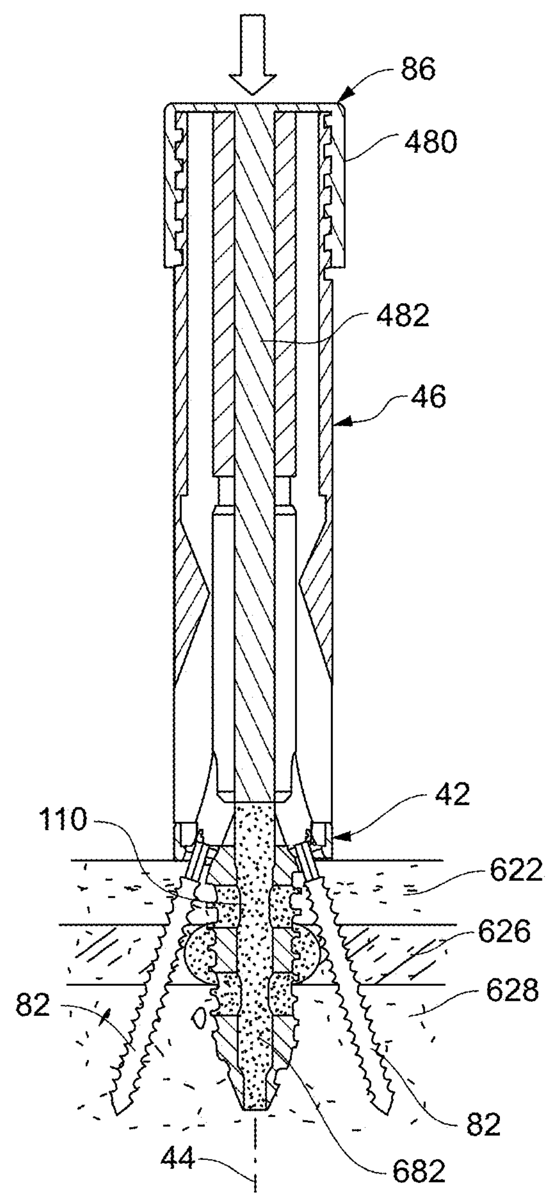
FIG. 53 is a sectional view of the plunger assembly of FIGS. 1 and 33 in operation to distribute grafting material for the fusion of the sacroiliac joint according to an embodiment of the disclosure.
Figure 54:
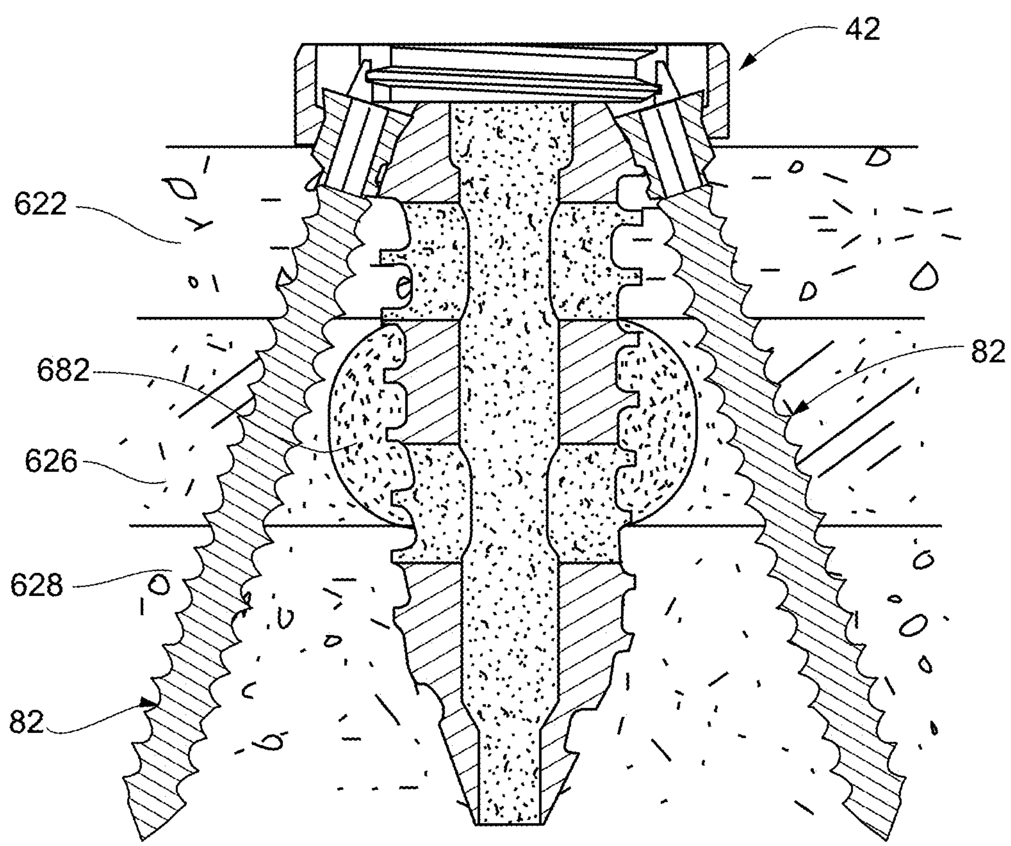
FIG. 54 is a sectional view of the primary screw and side screws implanted for fusion of a sacroiliac joint according to an embodiment of the disclosure.
Figure 55:
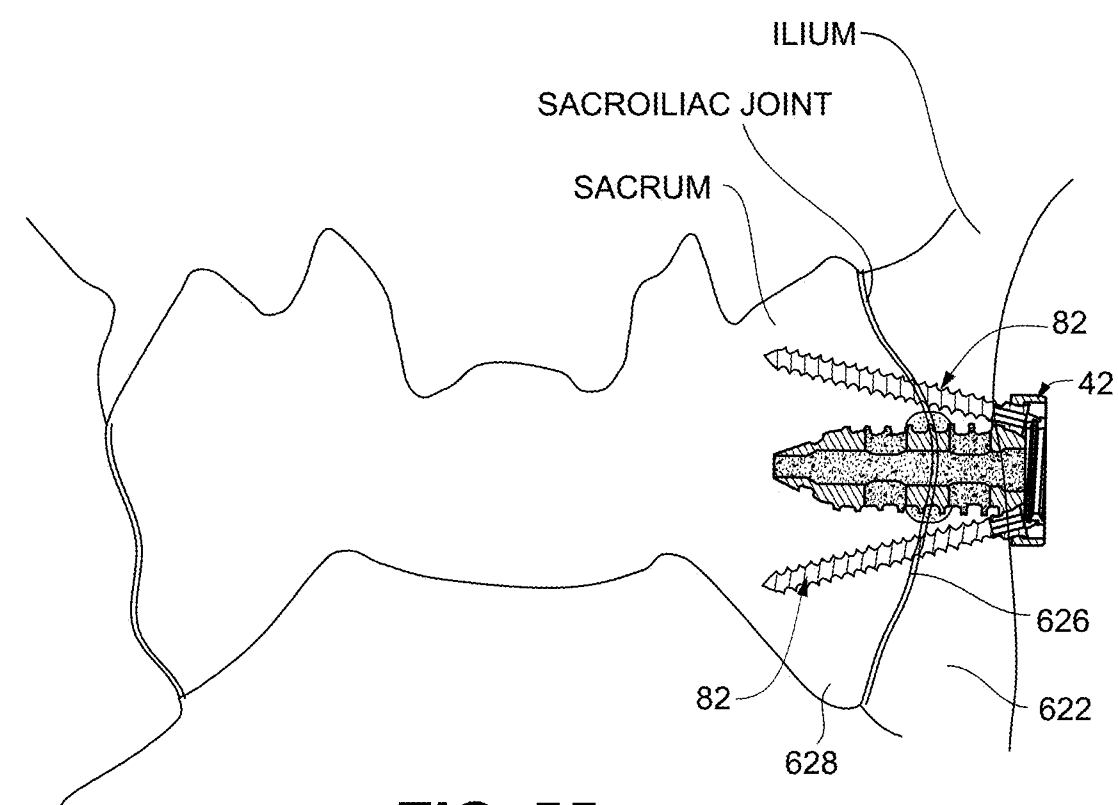
FIG. 55 is a sectional view of the primary screw and side screws of FIG. 54 implanted a sacroiliac joint according to an embodiment of the disclosure.

A portion of the tissue dislodged by the self-tapping primary screw 42 and the cutting action of the blades 62 may be internalized or drawn into the primary screw 42, for example by the rotating action of the blades 62 and the elongate side ports 112, as well as by retraction of the blades 62 back into the elongate side ports 112. Bone grafting material 682 may be injected into the primary screw 42 and the interior chamber 280, for example with a syringe 684 (FIG. 52). In some embodiments, the bone grafting material 682 is distributed and packed into the zone 632 via the side ports 112, 114 using the plunger assembly 86. The plunger stem 482 is inserted through the mirrored central arcuate channels 266 and into the interior chamber 280 of the inserter 46. The cap 480 is then threaded onto the external threads 230 of the main cylinder 220 to drive the plunger stem 482 into the bone grafting material 682, thereby pressurizing and packing the bone grafting material 682 into the zone 632 as well as the interior chamber 110 of the primary screw 42 (FIG. 53). The inserter 46 and plunger assembly 86 may be removed from the primary screw 42 by rotating the inserter 46 counterclockwise about the central axis 44 to decouple the exterior thread 232 of the boss 228 from the interior thread 138 of the recess 134 of the primary screw 42. The final, implanted assembly is left behind, as depicted in FIGS. 54 and 55.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, uncombined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

Unless indicated otherwise, references to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. A system for fusion of a sacroiliac joint, comprising:

a primary screw defining a central axis and defining a side screw port that extends along a side screw port axis, said side screw port axis intersecting said central axis at an acute angle;

a side screw that selectively couples to said primary screw; and an inserter defining an inserter axis that extends from a proximal end through a distal end, said distal end being selectively coupled to said primary screw, said inserter axis and said central axis of said primary screw being concentric when said inserter is selectively coupled to said primary screw, said inserter defining a side channel that extends from said proximal end and parallel to and radially offset from said inserter axis, said side channel being accessible from a lateral side of said inserter, said inserter defining a cross passage that extends along a canted axis from said side channel through a side egress port defined at a distal end of said inserter, said cross passage intersecting said central axis, wherein said canted axis of said inserter is concentric with said side screw port axis of said primary screw when said inserter is selectively coupled to said primary screw, and wherein said side channel and said cross passage are configured for passage of said side screw.

2. The system of claim 1, wherein said primary screw defines an interior chamber that extends along said central axis and defines a first opening about said central axis at a proximal end of said primary screw and a second opening about said central axis at a distal extremity of said primary screw, said second opening being configured to pass a guide rod.

3. The system of claim 2, wherein said primary screw defines an elongate side port that passes through a side wall of said primary screw and is in fluid communication with said interior chamber.

4. The system of claim 3, comprising a flexible blade disposed within said interior chamber of said shaft portion, said flexible blade extending axially and being tangentially aligned with said elongate side port, said flexible blade being configured to extend adjacent to an exterior opening of said elongate side port when in a retracted configuration, said flexible blade being configured to bow radially outward through said exterior opening of said elongate side port when in a deployed configuration.

5. The system of claim 1, wherein said side channel defines an arcuate cross section.

6. The system of claim 2, wherein said inserter defines an access slot that passes laterally through said inserter and is coplanar with said inserter axis, said access slot bifurcating said proximal end of said inserter into two opposed wall portions.

* * * * *